United States Patent
Wasserman

(10) Patent No.: US 12,119,759 B2
(45) Date of Patent: *Oct. 15, 2024

(54) HIGH VOLTAGE, HIGH EFFICIENCY SINE WAVE GENERATOR THAT PREVENTS SPIKES DURING AMPLITUDE ADJUSTMENTS AND SWITCHING OF CHANNELS

(71) Applicant: Novocure GmbH, Root (CH)

(72) Inventor: Yoram Wasserman, Haifa (IL)

(73) Assignee: Novocure GmbH, Root (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/105,069

(22) Filed: Feb. 2, 2023

(65) Prior Publication Data

US 2023/0188055 A1 Jun. 15, 2023

Related U.S. Application Data

(63) Continuation of application No. 17/125,362, filed on Dec. 17, 2020, now Pat. No. 11,601,067.

(Continued)

(51) Int. Cl.
*H02M 7/5387* (2007.01)
*A61N 1/32* (2006.01)
(Continued)

(52) U.S. Cl.
CPC ........ *H02M 7/53871* (2013.01); *A61N 1/326* (2013.01); *A61N 1/40* (2013.01); *G06F 1/022* (2013.01); *H02M 7/53878* (2021.05)

(58) Field of Classification Search
CPC ......... H02M 7/53871; H02M 7/53878; H02M 1/0012; H02M 1/007; A61N 1/326;
(Continued)

(56) References Cited

U.S. PATENT DOCUMENTS

| 6,868,289 B2 | 3/2005 | Palti |
| 7,016,725 B2 | 3/2006 | Palti |

(Continued)

FOREIGN PATENT DOCUMENTS

CA 2942319 C 11/2018

OTHER PUBLICATIONS

International Search Report and Written Opinion issued in application No. PCT/IB2020/062147 dated Sep. 16, 2021.

(Continued)

*Primary Examiner* — Mark W. Bockelman
(74) *Attorney, Agent, or Firm* — Potomac Law Group, PLLC

(57) ABSTRACT

This application describes a variety of approaches for generating high voltage sinusoidal signals whose output voltage can be adjusted rapidly, without introducing high-frequency artifacts on the output. When these approaches are used, stronger electric fields can be applied to the tumor for a higher percentage of time, which can increase the efficacy of TTFields therapy. In some embodiments, this is accomplished by preventing adjustments to a DC power source during times when the output of that DC power source is powering the output signal. In some embodiments, this is accomplished by synchronizing the operation of an AC voltage generator and an electronic switch that is connected to the output of the AC voltage generator.

19 Claims, 16 Drawing Sheets

Related U.S. Application Data

(60) Provisional application No. 62/981,875, filed on Feb. 26, 2020, provisional application No. 62/955,673, filed on Dec. 31, 2019.

(51) Int. Cl.
 *A61N 1/40* (2006.01)
 *G06F 1/02* (2006.01)

(58) Field of Classification Search
 CPC .... A61N 1/40; A61N 1/0476; A61N 1/36034; A61N 1/36002; G06F 1/022
 See application file for complete search history.

(56) References Cited

U.S. PATENT DOCUMENTS

| | | |
|---|---|---|
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Paiti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 10,953,209 B2 | 3/2021 | Story et al. |
| 11,020,585 B2 | 6/2021 | Alon et al. |
| 11,601,067 B2 * | 3/2023 | Wasserman ......... H02M 1/0012 |
| 2005/0209640 A1 | 9/2005 | Palti |
| 2006/0167499 A1 | 7/2006 | Palti |
| 2006/0282122 A1 | 12/2006 | Palti |
| 2007/0033660 A1 | 2/2007 | Palti |
| 2007/0225766 A1 | 9/2007 | Palti |
| 2007/0239213 A1 | 10/2007 | Palti |
| 2009/0076366 A1 | 3/2009 | Palti |
| 2011/0137229 A1 | 6/2011 | Palti et al. |
| 2012/0283726 A1 | 11/2012 | Palti |
| 2013/0178819 A1 | 7/2013 | Palti et al. |
| 2013/0178820 A1 | 7/2013 | Palti et al. |
| 2013/0184637 A1 | 7/2013 | Palti |
| 2013/0184674 A1 | 7/2013 | Palti |
| 2014/0330268 A1 | 11/2014 | Palti et al. |
| 2017/0093277 A1 | 3/2017 | Wasserman et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0114142 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2020/0368525 A1 | 11/2020 | Maag et al. |
| 2021/0000528 A1 | 1/2021 | Palti et al. |
| 2021/0008367 A1 | 1/2021 | Giladi et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |

OTHER PUBLICATIONS

Partial International Search Report and Invitation to Pay Additional fees issued in application No. PCT/IB2020/062147 dated Apr. 13, 2021.

* cited by examiner

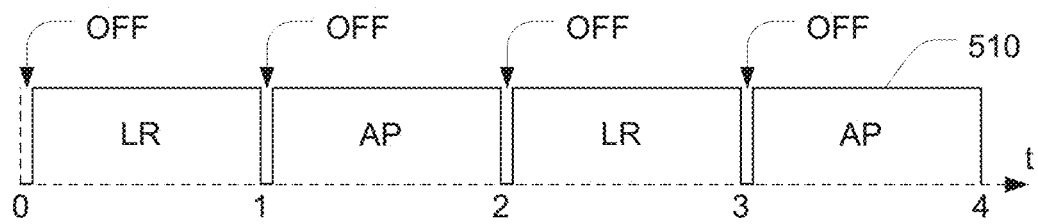
PRIOR ART  FIG. 14
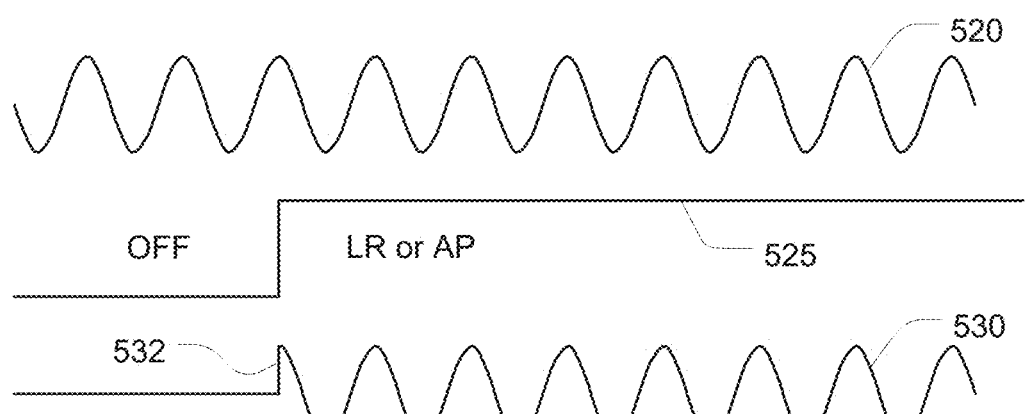
FIG. 15

HIGH VOLTAGE, HIGH EFFICIENCY SINE WAVE GENERATOR THAT PREVENTS SPIKES DURING AMPLITUDE ADJUSTMENTS AND SWITCHING OF CHANNELS

CROSS REFERENCE TO RELATED APPLICATIONS

This Application is a continuation of U.S. application Ser. No. 17/125,362, filed Dec. 17, 2020, which claims the benefit of U.S. Provisional Applications 62/955,673, filed Dec. 31, 2019, and 62/981,875, filed Feb. 26, 2020, each of which is incorporated herein by reference in its entirety.

BACKGROUND

Using TTFields therapy to treat tumors is described in U.S. Pat. No. 7,805,201. TTFields therapy makes use of high voltage sinusoidal signals. Originally, these high voltage sinusoidal signals were obtained by generating a low amplitude signal with a function generator, amplifying the low-voltage signal into a high-voltage signal using a linear amplifier, and subsequently applying the high-voltage signal to a set of electrodes (also referred to as transducer arrays) positioned on the patient's body. U.S. Pat. No. 9,910,453 describes an alternative approach for generating the high voltage sinusoidal signals that are applied to the transducer arrays, and this alternative approach provides dramatically improved efficiency with respect to the original linear amplifier approach.

SUMMARY OF THE INVENTION

This application describes a variety of approaches for generating high voltage sinusoidal signals whose output voltage can be adjusted rapidly, without introducing high-frequency artifacts (e.g., voltage spikes) on the output. When these approaches are used, stronger electric fields can be applied to the tumor for a higher percentage of time, which can increase the efficacy of the TTFields therapy.

One aspect of the invention is directed to a first apparatus for generating a sinusoid at a frequency f. The first apparatus comprises a DC power source having a voltage-control input that sets an output voltage of the DC power source; a transformer having a primary and a secondary; and a power switch. The power switch has a control input, and the power switch is configured to apply the output of the DC power source to the primary of the transformer in a first direction when a first control signal is applied to the control input, apply the output of the DC power source to the primary of the transformer in a second direction when a second control signal is applied to the control input, and remain off when neither the first control signal nor the second control signal is applied to the control input. The second direction is opposite to the first direction. The first apparatus also comprises a controller programmed to (a) apply the first control signal to the control input for a duration of T/3, then (b) wait for a duration of T/6, then (c) apply the second control signal to the control input for a duration of T/3, and then (d) wait for a duration of T/6, then continuously repeat the sequence (a), (b), (c), and (d). T is the reciprocal of the frequency f. And the first apparatus also comprises an output filter connected to the secondary of the transformer, wherein the output filter passes the frequency f and attenuates frequencies above a cut-off frequency. The controller is further programmed to control an amplitude of the sinusoid at the frequency by adjusting a third control signal that is applied to the voltage-control input of the DC power source, and the controller is further programmed to prevent adjustments of the third control signal from occurring when either the first control signal or the second control signal is being applied to the control input.

In some embodiments of the first apparatus, the cut-off frequency is between 2f and 4f and the output filter has a transfer function with a zero at 5f.

Another aspect of the invention is directed to a second apparatus for generating a sinusoid at a frequency f. The second apparatus comprises n DC power sources, each of the n DC power sources having a voltage-control input that sets an output voltage of the respective power source, where n is a positive integer. The second apparatus also comprises a power switch having output terminals and a control input. The power switch is configured to either (a) route the output of a selected one of the n DC power sources to the output terminals with a selected polarity in response to 2n states of a control signal that is applied to the control input or (b) remain off in response to an additional state of the control signal. The second apparatus also comprises a controller programmed to control the generation of an oversampled version of a sine wave that is sampled N times per cycle using evenly spaced samples that include a sampling point at 0°, where N=2+4n, by setting the output voltages of the n DC power sources to levels that are present on the oversampled version of the sine wave, and then sequencing the control signal through the 2n states and the additional state, so that each of the n DC power sources is routed to the output terminals of the power switch with the selected polarity at appropriate times in a sequence so as to generate the oversampled version of the sine wave. And the second apparatus also comprises an output filter that filters current arriving from the output terminals of the power switch. The output filter passes the frequency f and attenuates frequencies above a cut-off frequency. The controller is programmed to control an amplitude of the sinusoid by adjusting the output voltages of the n DC power sources via the voltage-control inputs, and the controller is further programmed not to adjust the output voltage of a DC power source while its output is being routed to the output terminals of the power switch.

Some embodiments of the second apparatus further comprise a transformer having a primary connected to the output terminals of the power switch and a secondary connected to the output filter, configured so that the current from the output terminals of the power switch arrives at the output filter via the transformer.

Some embodiments of the second apparatus further comprise a transformer having a primary connected to the output terminals of the power switch and a secondary connected to the output filter, configured so that the current from the output terminals of the power switch arrives at the output filter via the transformer. In these embodiments, n=1, which means that there is only a single DC power source. In these embodiments, the controller is programmed to control the generation of the oversampled version of the sine wave by (a) applying a first control signal to the control input for a duration of T/3 in order to cause the power switch to route the output of the single DC power source to the output terminals with a first polarity, then (b) waiting for a duration of T/6, then (c) applying a second control signal to the control input for a duration of T/3 in order to cause the power switch to route the output of the single DC power source to the output terminals with a second polarity that is opposite to the first polarity, and then (d) waiting for a duration of T/6, then continuously repeating the sequence (a), (b), (c), and (d). T is the reciprocal of the frequency f. Optionally, in these embodiments, the cut-off frequency is between 2f and 4f, and the output filter has a transfer function with a zero at 5f.

In some embodiments of the second apparatus, n>1; and the controller is further programmed to control an amplitude of the sinusoid by adjusting the output voltages of the n DC power sources via the voltage-control inputs, while maintaining a fixed ratio between the output voltages of each of the n DC power sources. Optionally, in these embodiments, the output filter may have a transfer function with a zero at a frequency where a harmonic of the frequency f is expected to contain power.

Another aspect of the invention is directed to a first method for generating a sinusoid at a frequency f. The first method comprises setting n DC power sources to respective output voltages, where n is a positive integer; and generating an oversampled version of a sine wave that is sampled N times per cycle using evenly spaced samples that include a sampling point at 0°, where N=2+4n, by setting the output voltages of the n DC power sources to levels that are present on the oversampled version of the sine wave, and then switching the outputs of the n DC power sources to an output in a controlled sequence such that each of the n DC power sources is switched to the output in each direction at appropriate times in the sequence so as to generate the oversampled version of the sine wave. The first method also comprises filtering the oversampled version of the sine wave to pass the frequency f and attenuate frequencies above a cut-off frequency, wherein the filtering implements a transfer function with a zero at a frequency where a harmonic of the frequency f is expected to contain power. The amplitude of the sinusoid is controlled by adjusting the output voltages of the n DC power sources, and adjustment of the output voltage of any given one of the DC power sources is prevented while the given one of the DC power sources is switched to the output.

In some instances of the first method, n=1, which means that there is only a single DC power source; and adjustment of the output voltage of the single DC power source only occurs during such times when the output of the single DC power source is not being switched to the output.

In some instances of the first method, the filtering implements a transfer function with a zero at a frequency where a harmonic of the frequency f is expected to contain power.

Another aspect of the invention is directed to a third apparatus for generating an output waveform at a frequency f The third apparatus comprises a first DC power source having a first voltage-control input that sets an output voltage of the first DC power source; and a second DC power source having a second voltage-control input that sets an output voltage of the second DC power source. The third apparatus also comprises a power switch having output terminals and a control input. The power switch is configured to (a) route the output of the first DC power source to the output terminals with a first polarity in response to a first state of the control input, (b) route the output of the first DC power source to the output terminals with a second polarity in response to a second state of the control input, (c) route the output of the second DC power source to the output terminals with the first polarity in response to a third state of the control input, (d) route the output of the second DC power source to the output terminals with the second polarity in response to a fourth state of the control input, and (e) remain off in response to an additional state of the control input. The second polarity is opposite to the first polarity.

The third apparatus also comprises an output filter that filters current arriving from the output terminals of the power switch. The output filter passes the frequency f and attenuates frequencies above a cut-off frequency. The third apparatus also comprises a controller programmed to operate in a first mode in which the controller sets the control input to the first and second states in an alternating sequence while holding the first voltage-control input constant. The controller is further programmed to operate in a second mode in which the controller sets the control input to the third and fourth states in an alternating sequence while holding the second voltage-control input constant. The controller is further programmed so that if the controller is operating in the first mode, the controller brings about changes in amplitude of the output waveform by adjusting the second voltage-control input and subsequently switching the controller to the second mode, and the controller is further programmed so that if the controller is operating in the second mode, the controller brings about changes in amplitude of the output waveform by adjusting the first voltage-control input and subsequently switching the controller to the first mode.

In some embodiments of the third apparatus, the output waveform is a sinusoid; the setting of the control input to the first and second states in the alternating sequence comprises (a) placing the control input in the first state for a duration of T/3, then (b) waiting for a duration of T/6, then (c) placing the control input in the second state for a duration of T/3, and then (d) waiting for a duration of T/6, then continuously repeating the sequence (a), (b), (c), and (d); the setting of the control input to the third and fourth states in the alternating sequence comprises (e) placing the control input in the third state for a duration of T/3, then (f) waiting for a duration of T/6, then (g) placing the control input in the fourth state for a duration of T/3, and then (h) waiting for a duration of T/6, then continuously repeating the sequence (e), (f), (g), and (h). T is the reciprocal of the frequency f.

In some embodiments of the third apparatus, the controller is further programmed so that if the controller is operating in the first mode, the controller brings about changes in amplitude of the output waveform by adjusting the second voltage-control input at least 1 ms before switching the controller to the second mode; and the controller is further programmed so that if the controller is operating in the second mode, the controller brings about changes in amplitude of the output waveform by adjusting the first voltage-control input at least 1 ms before switching the controller to the first mode.

Some embodiments of the third apparatus further comprise a transformer having a primary connected to the output terminals of the power switch and a secondary connected to the output filter, configured so that the current from the output terminals of the power switch arrives at the output filter via the transformer. Optionally, in these embodiments, the power switch may be configured to (a) route the output of the first DC power source to the primary of the transformer in a first direction in response to the first state of the control input, (b) route the output of the first DC power source to the primary of the transformer in a second direction in response to the second state of the control input, (c) route the output of the second DC power source to the primary of the transformer in the first direction in response to the third state of the control input, (d) route the output of the second DC power source to the primary of the transformer in the second direction in response to the fourth state of the control input, and (e) remain off in response to a fifth state of the control input. The second direction is opposite to the first direction.

In some embodiments of the third apparatus, the cut-off frequency is between 2f and 4f, and the output filter has a transfer function with a zero at 5f.

Another aspect of the invention is directed to a second method for generating an output waveform at a frequency f. The second method comprises routing an output of a first DC power source to output terminals of a power switch with a first polarity in response to a first state of a control input of the power switch, (b) routing the output of the first DC power source to the output terminals with a second polarity in response to a second state of the control input, (c) routing the output of a second DC power source to the output terminals with the first polarity in response to a third state of the control input, (d) routing the output of the second DC power source to the output terminals with the second polarity in response to a fourth state of the control input, and (e) remaining off in response to an additional state of the control input. The second polarity is opposite to the first polarity. The second method also comprises filtering current arriving from the output terminals of the power switch. The filtering comprises passing the frequency f and attenuating frequencies above a cut-off frequency. The second method also comprises operating in a first mode in which the control input is set to the first and second states in an alternating sequence while holding the output voltage of the first DC power source constant. The second method also comprises operating in a second mode in which the control input is set to the third and fourth states in an alternating sequence while holding the output voltage of the second DC power source constant. In the first mode, changes in amplitude of the output waveform are brought about by adjusting the output voltage of the second DC power source and subsequently switching to the second mode. And in the second mode, changes in amplitude of the output waveform are brought about by adjusting the output voltage of the first DC power source and subsequently switching to the first mode.

In some instances of the second method, the output waveform is a sinusoid, and the control input is set to the first and second states in the alternating sequence by (a) placing the control input in the first state for a duration of T/3, then (b) waiting for a duration of T/6, then (c) placing the control input in the second state for a duration of T/3, and then (d) waiting for a duration of T/6, then continuously repeating the sequence (a), (b), (c), and (d). In these instances, the control input is set to the third and fourth states in the alternating sequence by (e) placing the control input in the third state for a duration of T/3, then (f) waiting for a duration of T/6, then (g) placing the control input in the fourth state for a duration of T/3, and then (h) waiting for a duration of T/6, then continuously repeating the sequence (e), (f), (g), and (h). And in these instances, T is the reciprocal of the frequency f.

In some instances of the second method, in the first mode, changes in amplitude of the output waveform are brought about by adjusting the output voltage of the second DC power source at least 1 ms before switching to the second mode; and in the second mode, changes in amplitude of the output waveform are brought about by adjusting the output voltage of the first DC power source at least 1 ms before switching to the first mode.

Another aspect of the invention is directed to a fourth apparatus for generating AC electrical signals for application to a first pair of electrodes and a second pair of electrodes. The fourth apparatus comprises an AC voltage generator having an output, and electronic switch, and a controller. The electronic switch has an input that receives the output of the AC voltage generator, a first power output, and a second power output. The electronic switch is configured to (a) operate in a first mode that routes the output of the AC voltage generator to the first power output, and (b) operate in a second mode that routes the output of the AC voltage generator to the second power output. The electronic switch is further configured to cycle through a repeating sequence that includes the first mode and the second mode. The controller is configured to synchronize the operation of the AC voltage generator and the electronic switch such that the instantaneous output of the AC voltage generator is less than 5 V in magnitude whenever the electronic switch switches to either the first mode or the second mode. Within 20 ms after the electronic switch switches to either the first mode or the second mode, the AC voltage generator's output voltage is at least 80% of the AC voltage generator's steady-state output voltage.

In some embodiments of the fourth apparatus, the electronic switch is further configured to (c) operate in a third mode in which the output of the AC voltage generator is not routed to either the first power output or the second power output, and (d) cycle through the first mode, the second mode, and the third mode in the following repeating sequence (1) first mode, (2) third mode, (3) second mode, and (4) third mode. In some embodiments of the fourth apparatus, the controller is configured to synchronize the operation of the AC voltage generator and the electronic switch such that the instantaneous output of the AC voltage generator is less than 1 V in magnitude whenever the electronic switch switches to either the first mode or the second mode.

In some embodiments of the fourth apparatus, within 5 ms after the electronic switch switches to either the first mode or the second mode, the AC voltage generator's output voltage is at least 80% of the AC voltage generator's steady-state output voltage. In some embodiments of the fourth apparatus, within 1 ms after the electronic switch switches to either the first mode or the second mode, the AC voltage generator's output voltage is at least 80% of the AC voltage generator's steady-state output voltage.

In some embodiments of the fourth apparatus, the AC voltage generator continues to operate at its full steady-state AC output voltage during transitions of the electronic switch to either the first mode or the second mode.

In some embodiments of the fourth apparatus, the controller synchronizes the operation of the AC voltage generator and the electronic switch by controlling timing of transitions of the electronic switch so that the transitions coincide with windows of time during which the instantaneous output of the AC voltage generator is less than 5 V in magnitude. In some embodiments of the fourth apparatus, the controller synchronizes the operation of the AC voltage generator and the electronic switch by controlling the AC voltage generator so that the output of the AC voltage generator is turned off whenever a transition of the electronic switch occurs. In some embodiments of the fourth apparatus, the controller synchronizes the operation of the AC voltage generator and the electronic switch by both (a) controlling timing of transitions of the electronic switch so that the transitions coincide with windows of time during which the instantaneous output of the AC voltage generator is less than 5 V in magnitude and (b) controlling the AC voltage generator so that the output of the AC voltage generator is turned off whenever a transition of the electronic switch occurs.

In some embodiments of the fourth apparatus, the electronic switch is configured to cycle through the first mode and the second mode in the following repeating sequence (1) first mode, (2) second mode. In these embodiments, the electronic switch is configured to switch directly from the first mode to the second mode and to switch directly from the second mode to the first mode.

Another aspect of the invention is directed to a fifth apparatus for generating AC electrical signals for application to a first pair of electrodes and a second pair of electrodes. The fifth apparatus comprises an AC voltage generator having an output, an electronic switch, and a controller. The electronic switch has an input that receives the output of the AC voltage generator, a first power output, and a second power output. The electronic switch is configured to (a) operate in a first mode that routes the output of the AC voltage generator to the first power output, and (b) operate in a second mode that routes the output of the AC voltage generator to the second power output. The electronic switch is further configured to cycle through a repeating sequence that includes the first mode and the second mode. The controller is configured to synchronize the operation of the AC voltage generator and the electronic switch such that whenever the electronic switch switches to either the first mode or the second mode, the instantaneous output of the AC voltage generator has a magnitude that is below a threshold at which a subject being treated begins to experience a perceptible sensation. Within 20 ms after the electronic switch switches to either the first mode or the second mode, the AC voltage generator's output voltage is at least 80% of the AC voltage generator's steady-state output voltage.

In some embodiments of the fifth apparatus, the electronic switch is further configured to (c) operate in a third mode in which the output of the AC voltage generator is not routed to either the first power output or the second power output, and (d) cycle through the first mode, the second mode, and the third mode in the following repeating sequence (1) first mode, (2) third mode, (3) second mode, and (4) third mode.

In some embodiments of the fifth apparatus, the controller is configured to synchronize the operation of the AC voltage generator and the electronic switch such that the instantaneous output of the AC voltage generator is less than 1 V in magnitude whenever the electronic switch switches to either the first mode or the second mode.

In some embodiments of the fifth apparatus, within 5 ms after the electronic switch switches to either the first mode or the second mode, the AC voltage generator's output voltage is at least 80% of the AC voltage generator's steady-state output voltage. In some embodiments of the fifth apparatus, within 1 ms after the electronic switch switches to either the first mode or the second mode, the AC voltage generator's output voltage is at least 80% of the AC voltage generator's steady-state output voltage.

In some embodiments of the fifth apparatus, the AC voltage generator continues to operate at its full steady-state AC output voltage during transitions of the electronic switch to either the first mode or the second mode.

In some embodiments of the fifth apparatus, the controller synchronizes the operation of the AC voltage generator and the electronic switch by controlling timing of transitions of the electronic switch so that the transitions coincide with windows of time during which the instantaneous output of the AC voltage generator has a magnitude that is below the threshold. In some embodiments of the fifth apparatus, the controller synchronizes the operation of the AC voltage generator and the electronic switch by controlling the AC voltage generator so that the output of the AC voltage generator is turned off whenever a transition of the electronic switch occurs. In some embodiments of the fifth apparatus, the controller synchronizes the operation of the AC voltage generator and the electronic switch by both (a) controlling timing of transitions of the electronic switch so that the transitions coincide with windows of time during which the instantaneous output of the AC voltage generator has a magnitude that is below the threshold and (b) controlling the AC voltage generator so that the output of the AC voltage generator is turned off whenever a transition of the electronic switch occurs.

In some embodiments of the fifth apparatus, the electronic switch is configured to cycle through the first mode and the second mode in the following repeating sequence (1) first mode, (2) second mode. In these embodiments, the electronic switch is configured to switch directly from the first mode to the second mode and to switch directly from the second mode to the first mode.

BRIEF DESCRIPTION OF THE DRAWINGS

FIG. 14 is a timing diagram that shows the sequencing between the two directions LR and AP that was used in the FIG. 13 prior art system.

FIG. 15 depicts a waveform that includes a significant spike.

Various embodiments are described in detail below with reference to the accompanying drawings, wherein like reference numerals represent like elements.

DESCRIPTION OF THE PREFERRED EMBODIMENTS

When using the prior art approaches to generate high voltage sinusoidal signals in connection with TTFields therapy, high-frequency artifacts (e.g., voltage spikes) may appear on the output under specific conditions (e.g., in response to a command to change the output voltage, or when the direction of the TTFields is switched). And because those high-frequency artifacts can create an unpleasant sensation in the person being treated with TTFields therapy, the output voltage amplitude was typically ramped-up slowly to prevent those high-frequency artifacts (and the resulting unpleasant sensations) from occurring. But using a slow ramp-up has a downside: the output voltage is not always as high as it could be, which means that the electric field being applied to the tumor is not always as strong as it could be. And when the electric field is not as strong as it could be, the efficacy of treatment can be reduced. The embodiments described herein can advantageously increase the output voltage amplitude much more rapidly, without introducing high-frequency artifacts. These embodiments can therefore prevent unpleasant sensations from occurring without incurring an associated decrease in efficacy of treatment.

The embodiments described herein are useful in connection with generating TTFields, as described in U.S. Pat. No. 7,805,201, which is incorporated herein by reference. The embodiments described herein build upon the architecture described in U.S. Pat. No. 9,910,453, which is incorporated herein by reference. Notably, the embodiments described herein enable the voltage of the sinusoidal signals (which are applied to the TTFields transducer arrays) to be adjusted more rapidly, without the risk of introducing high-frequency artifacts (e.g., voltage spikes) on the output. The embodiments described herein also enable the sinusoidal signals to be switched on and off to full power instantaneously, without the risk of introducing high-frequency artifacts on the output.

Note that when generating a high-voltage signal for TTFields delivery, the exact shape of the signal is known at every moment (pure sine wave at a known frequency) and it is only the amplitude of the output signal that changes over time, based on external inputs (e.g., control based on the skin temperature of the patient).

The embodiments described herein generate high voltage sinusoidal signals by generating a specific pulse train that, when filtered using a specific low pass filter, will result in a low distortion sine wave of the desired amplitude and frequency.

Figure 1:
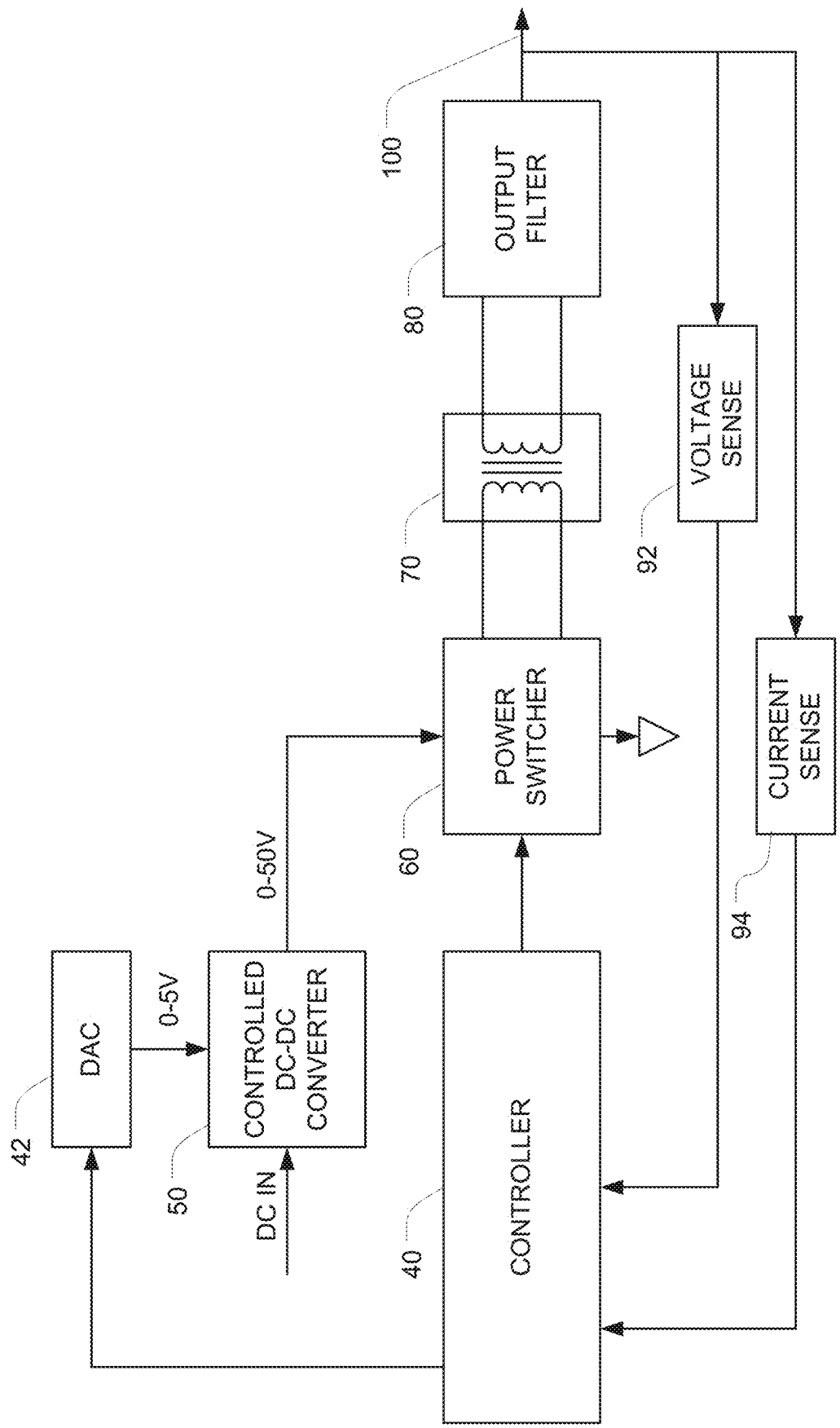
FIG. 1 is a block diagram of a first embodiment of a sinusoid generator that generates a sinusoid at a pre-set frequency f, with a controllable amplitude.

FIG. 1 is a block diagram of a first embodiment of a sinusoid generator that generates a sinusoid at a pre-set frequency f, with a controllable amplitude. Ultimately, the amplitude of the output sinusoid will be proportional to the output of the DC power source 50, which is preferably a controlled DC-DC converter.

In the illustrated embodiment, the DC to DC converter 50 is configured to multiply an analog voltage-control input signal by 10, so when a 1 V voltage-control signal is applied the output will be 10 V, and when a 5 V voltage-control signal is applied the output will be 50 V, with proportional control therebetween. The output of the DC-DC converter 50 can therefore take any value between 0 and 50 V, depending on the voltage (e.g., 0-5 V) that is applied to the analog voltage-control input. A controller 40 controls the output voltage of the DC-DC converter 50 by writing a control word to a digital-to-analog converter (DAC) 42. The DAC 42 then generates an analog voltage that is proportional to the control word, and this analog voltage is applied to the voltage-control input of the DC-DC converter 50.

The output of the DC-DC converter 50 is routed to the power switcher 60. The power switcher 60 has a control input, and depending on the state of the control input, it will route the output of the DC-DC converter 50 to the primary of the transformer 70 in either direction. More specifically, when a first control signal is applied to the control input, the power switcher 60 will apply the output of the DC-DC converter 50 to the primary of the transformer 70 in a first direction. When a second control signal is applied to the control input, the power switcher 60 will apply the output of the DC-DC converter 50 to the primary of the transformer 70 in a second direction that is opposite to the first direction. When neither the first control signal nor the second control signal is applied to the control input, the power switcher 60 will remain off, in which case power from the DC-DC converter 50 is not routed to the primary of the transformer 70.

Figure 2:
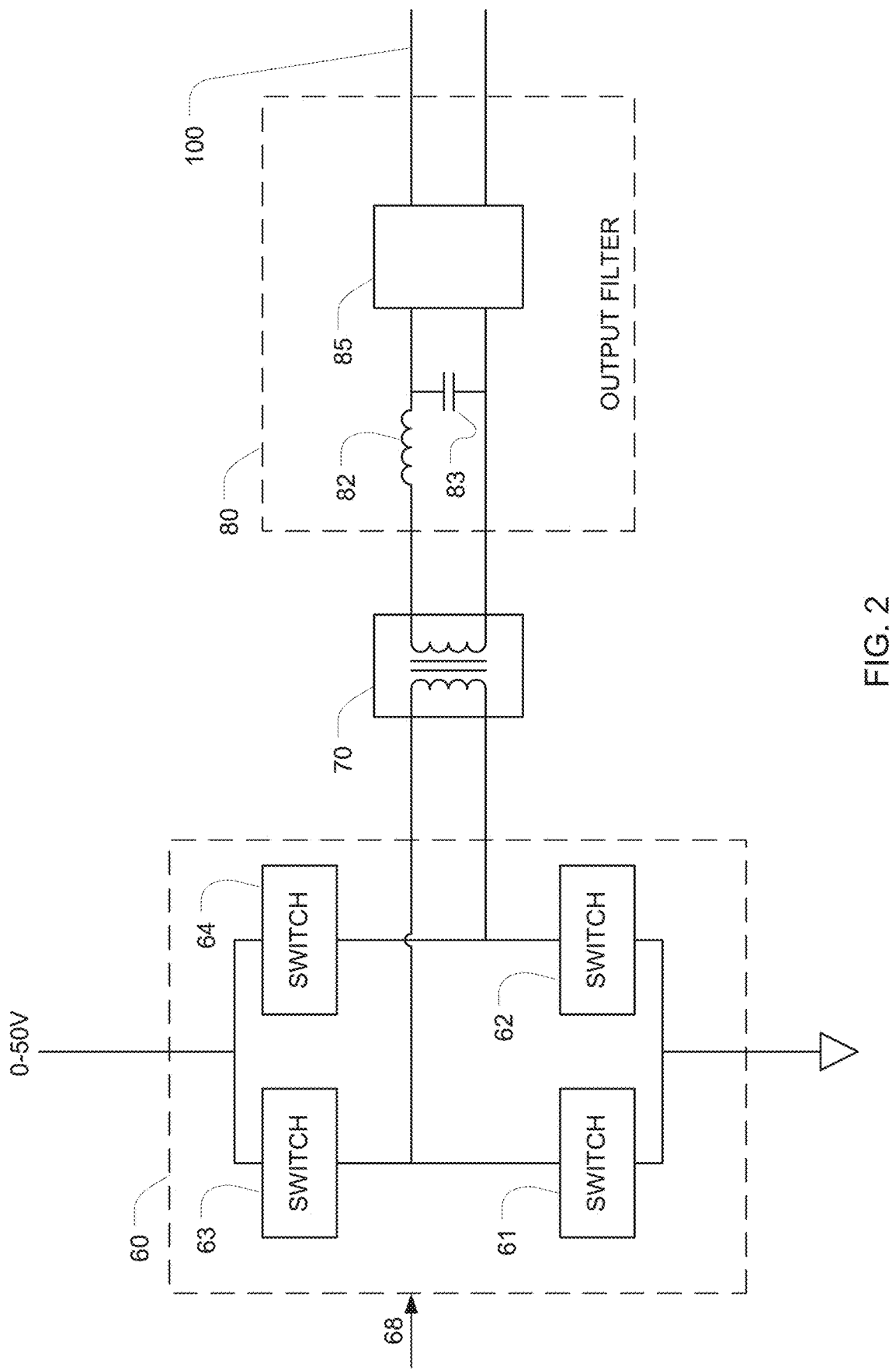
FIG. 2 depicts a block diagram of one preferred approach for implementing the power switcher and a suitable architecture for implementing the output filter.

FIG. 2 includes a block diagram of one preferred approach for implementing the power switcher 60 using a set of four electronically controlled switches 61-64 connected to the primary of the transformer 70 in an H-bridge configuration. These switches 61-64 open and close in response to signals that are applied to a control input 68. A wide variety of technologies may be used for implementing these switches, as will be appreciated by persons skilled in the relevant arts. For example, the switches 61-64 may be implemented using MOSFET transistors (e.g., BSC109N10NS3 manufactured by Infineon) along with appropriate logic to switch them on and off in response to a control signal. In order to apply the output of the DC-DC converter 50 to the primary of the transformer 70 in the first direction, only switches 63 and 62 should be closed. In order to apply the output of the DC-DC converter 50 to the primary of the transformer 70 in the opposite direction, only switches 61 and 64 should be closed. When all four of these switches 61-64 are off, no power is routed into the primary of the transformer 70.

Transformer 70 is preferably a step-up transformer with a step-up ratio between 1:4 and 1:9. In some preferred embodiments, transformer 70 is a step-up transformer with a step-up ratio of 1:6. For example, when a transformer with a 1:6 step-up ratio is used in combination with a DC-DC converter 50 that can output up to 24 V, the resulting voltage at the secondary of the transformer 70 can go as high as 300 V.

Figure 3:
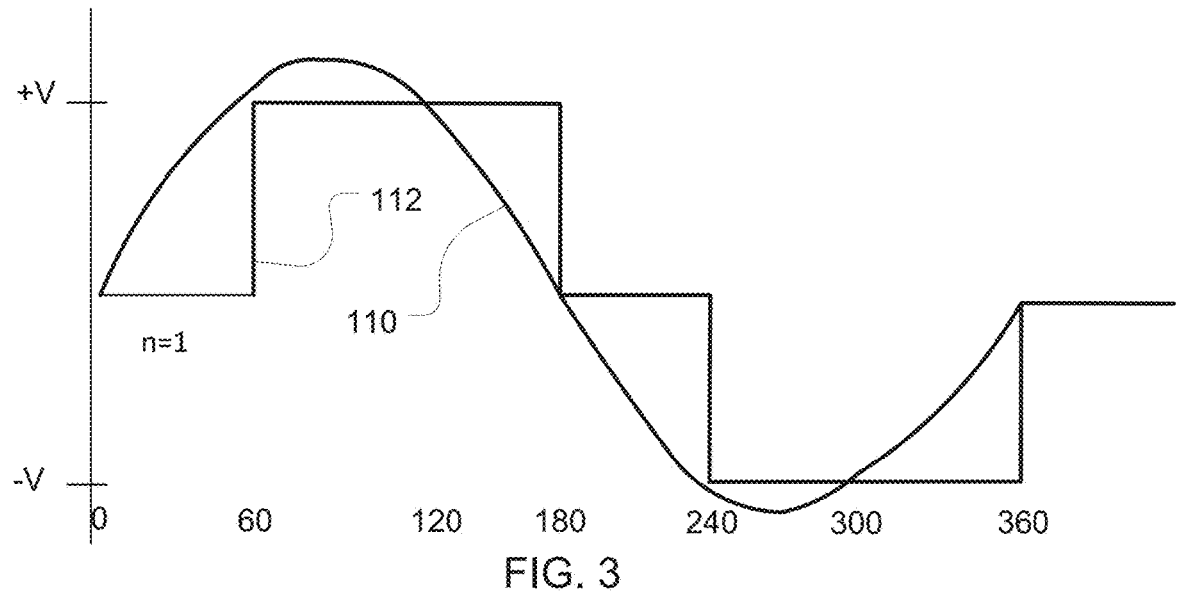
FIG. 3 depicts a sine wave and an oversampled version of that sine wave that is sampled 6 times per cycle.

Returning to FIG. 1, the controller 40 applies control signals to the control input of the power switcher 60 in a time-choreographed sequence in order to construct an oversampled version of a sine wave that is sampled six times per cycle using evenly spaced samples. More specifically, FIG. 3 depicts a sine wave 110 and an oversampled version of that sine wave 112 that is sampled at 0°, 60°, 120°, 180°, 240°, 300°, and 360°. Looking at this oversampled version 112, it becomes apparent that it contains only three voltage levels: a positive voltage +V between 60° and 180°, a negative voltage −V between 240° and 360°, and zero volts between 0° and 60° and also between 180° and 240°. Note that the zero Volt level exists because we have chosen the sampling times such that one of the sampling points occurs at 0° and another one of the sampling points occurs at 180°, where the sine function equals zero. This choice advantageously reduces the number of voltage levels that must be generated to construct the oversampled version 112 of the sine wave. It also advantageously reduces the number of switching events, which minimizes losses that are incurred during the switching process.

As a result, an oversampled version of a sinusoid at a pre-set frequency f can be constructed at the output of the transformer 70 by continuously repeating the following four steps: (a) applying the first control signal to the control input 68 for a duration of T/3, which corresponds to the 60-180° segment of waveform 112 in FIG. 3; then (b) waiting for a duration of T/6, which corresponds to the 180-240° segment of waveform 112; then (c) applying the second control signal to the control input 68 for a duration of T/3, which corresponds to the 240-360° segment of waveform 112; and then (d) waiting for a duration of T/6, which corresponds to the 0-60° segment of waveform 112. Note that T is the reciprocal of the pre-set frequency f The controller 40 is responsible for generating these control signals in this sequence. The controller 40 may be implemented using a wide variety of approaches that will be apparent to persons skilled in the relevant arts including but not limited to a microcontroller or microprocessor that has been programmed to perform the functions described herein. The controller 40 may also be implemented using a microcontroller or microprocessor combined with a hardwired sequencer, the latter of which may be implemented using, for example, a state machine or a counter.

The output of the secondary of the transformer 70 is routed to an output filter 80 that has a cut-off frequency between 2f and 4f The output filter 80 passes the pre-set frequency f and attenuates frequencies above the cutoff frequency.

Note that when the oversampled version of the sine wave (112 in FIG. 3) is converted to the frequency domain, all of the even harmonics will be zero as a result of the fact that waveform 112 being symmetric. In addition, because sampling is performed 6 times per period, the third harmonic of waveform 112 will also be zero.

Many filter designs have inherent instabilities at their cutoff frequencies. But because the third harmonic component of the oversampled waveform 112 is zero, the lowest harmonic that will have any significant power will be the fifth harmonic. If the output filter 80 is designed so that its cutoff frequency coincides with the third harmonic, the oversampled waveform 112 will not be affected by the instabilities in the vicinity of the cutoff frequency, because the waveform contains no power at 3f. It is therefore most preferable to design the output filter 80 with its cutoff frequency at 3f, in which case (a) the fundamental component will be far enough below the cutoff frequency so as not to activate the instabilities and (b) the fifth harmonic will be far enough above the cutoff frequency so as not to activate the instabilities.

To further reduce the higher order harmonics, the output filter 80 is preferably designed so that the transfer function of the output filter has a zero located at the fifth harmonic. This may be accomplished, for example, by selecting the components within the output filter 80 to implement an elliptic low pass filter or a Chebyshev-2 low pass filter. Ordinarily, elliptic filters and Chebyshev-2 filters are not suitable for filtering square waves into sine waves because they have significant ripple in the stop band. As a result, if an incoming signal happens to contain a frequency component that coincides with a crest within that ripple, that component would not be filtered out from the incoming signal. The FIG. 1 embodiment avoids this situation by generating the oversampled waveform 112 at a pre-set frequency, which means that the frequency of the fifth harmonic will be known in advance. By selecting the components within the output filter 80 so that its transfer function has a zero at the fifth harmonic, we ensure that the fifth harmonic will never coincide with a crest within the ripple in the stop band.

To reduce the higher harmonics even further, the output filter 80 may be designed so that its transfer function has an additional zero located at the seventh harmonic. Here again, because the frequency of the seventh harmonic will be known in advance, the components within the output filter 80 can be selected so that its transfer function has a zero at the seventh harmonic.

Designing the output filter 80 with zeros at the fifth and seventh harmonics reduces the attenuation at other frequencies located between the harmonics, which would ordinarily be very undesirable. However, because the frequency of the oversampled waveform 112 is pre-set in advance and because it only contains signals centered around the odd harmonics (starting with the fifth harmonic), this design will actually decrease the overall distortion of the output signal in the FIG. 1 embodiment.

When the output filter 80 is designed with zeros at the fifth and seventh harmonics, the initial harmonic that will contain any significant power will be the ninth harmonic. But because the power in the ninth harmonic of the oversampled waveform 112 (in FIG. 3) is relatively low to begin with, and because the ninth harmonic is 6f above the cutoff frequency, the power in the ninth harmonic (and all higher harmonics) at the output 100 of the output filter 80 will be low enough to produce an excellent sine wave.

FIG. 2 depicts a suitable architecture for implementing the output filter 80 with the cutoff frequency and the zeros at the locations indicated above. Preferably, the output filter 80 is a multi-stage low pass LC filter. In this case, the first stage of the output filter 80 comprises inductor 82 and capacitor 83, and the subsequent stages are represented by block 85. In some embodiments, the filter 80 is a fourth order LC low pass filter. In some embodiments, the filter 80 is a dual M-type element low pass filter.

When the electrical characteristics of transformer 70 are modelled, the leakage inductance of the transformer appears in series with the secondary of transformer 70. As a result, this leakage inductance must be accounted for when calculating the inductance of the first inductor 82 in the first stage of the output filter 80. In some embodiments, a transformer 70 with a leakage inductance that is large enough to supply all of the inductance that is needed for the first inductor 82 is selected. In this case, the first inductor 82 can be eliminated entirely from the output filter 80 and replaced with a wire. For example, if the calculated desired value for the first inductor in the output filter is 60 μH and the leakage inductance of the transformer 70 is 60 μH, the first inductor 82 of the output filter can be eliminated entirely.

In alternative embodiments, the leakage inductance of the transformer 70 accounts for at least half of the inductance of the first stage of the low pass LC filter. In these embodiments, we start with the calculated value for the first inductor 82 and reduce that value by the leakage inductance of the transformer 70. For example, if the calculated value for the first inductor in the first stage of the output filter is 100 μH and the leakage inductance of the transformer 70 is 60 μH, a 40 μH inductor should be used as the first inductor 82 of the output filter (because 100 μH−60 μH=40 μH).

Figure 4:
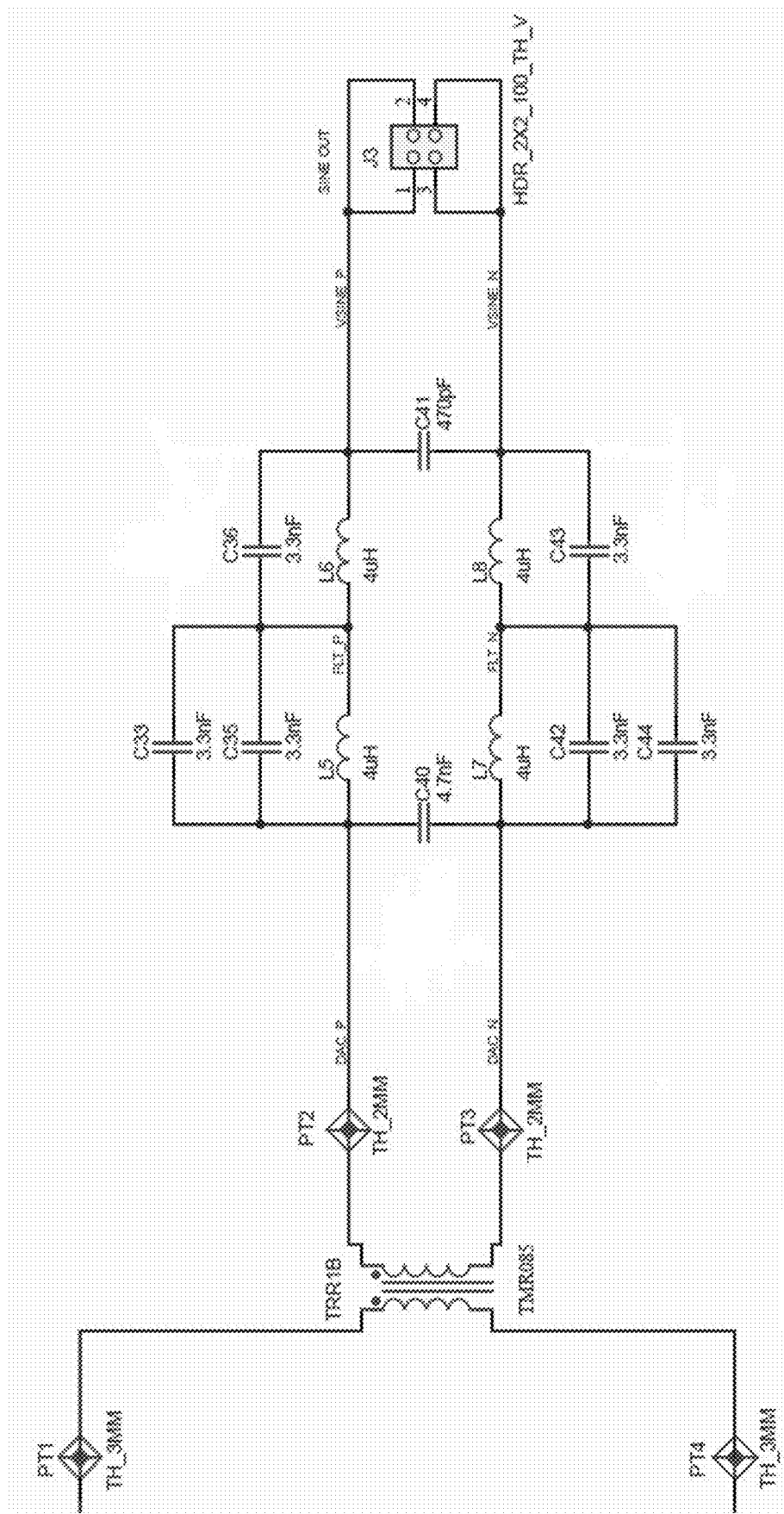
FIG. 4 is a schematic diagram of an embodiment of the output filter.

FIG. 4 is a schematic diagram of an embodiment of the output filter 80 in which the inductance of the transformer 70 provides all of the inductance that is needed to serve as the first inductor for the first stage of the output filter. The transformer in FIG. 4 is a Zolotov TRM085, which has the following characteristics: a turn ratio of 6:25; an inductance of 0.25 mH in the primary (at 200 kHz); an inductance of 4.5 mH in the secondary (at 200 kHz); and a leakage inductance between 32 and 36 μH (at 200 kHz). The capacitors C33, C35, C36, C42, C43, and C44 are all 3300 pF capacitors. C40 is a 4.7 nF capacitor. C41 is a 470 pF capacitor. The inductor L5-L8 are all 4 μH inductors. The values of these components were selected to position the zeros of the filter at the fifth harmonic and the seventh harmonic when the operating frequency is 200 kHz.

An alternative design for implementing an output filter 80 with an operating frequency of 150 kHz can be realized by starting with the schematic of FIG. 4 and (a) adding an additional 4.7 nF capacitor in parallel with C40; and (b) swapping in 5600 pF capacitors in place of the 3300 pF capacitors C33, C35, C36, C42, C43, and C44. These components were selected to position the zeros of the filter at the fifth harmonic and the seventh harmonic when the operating frequency is 150 kHz.

The output impedance of the output filter 80 is preferably as close as possible to 70 ohms. In alternative embodiments, the output impedance of the output filter 80 is between 40 and 120 ohms. Using an output impedance in this range is appropriate because the current and voltage of the output signal 100 can change depending on the load that is presented (i.e., the patient and the transducer arrays in the context of TTFields treatments). But because the output impedance is between 40 and 120 ohms, even if there is a short circuit on the exit, the current will not surge to dangerous values. In addition, if the impedance of the load suddenly increases (e.g., if an electrode becomes partially disconnected from a patient), then the drop in current will be a lot less significant. This is very useful as a safety feature in the context of TTFields treatment.

The controller 40 controls the amplitude of the output signal 100 by adjusting the control signal that is applied to the voltage control input of the DC-DC converter 50. In the illustrated embodiment, this is accomplished by having the controller 40 write a control word to the DAC 42. The DAC 42 responds by outputting an analog voltage, which serves as the control signal that is applied to the voltage-control input of the DC-DC converter 50. Assume, for example, that the output of the DAC 42 starts at 1 V, that the DC-DC converter is outputting 10 VDC, and that the transformer 70 has a step-up ratio of 1:6. Under these conditions, the pulses at the output of the secondary of the transformer 70 will be 60 V. When the controller 40 writes a new control word to the DAC 42 that causes the output of the DAC 42 to increase to 2 V. The DC-DC converter 50 will respond to the new signal that is being applied to its voltage-control input by increasing its output voltage to 20 V DC, which (after passing through the step up transformer 70) will cause the pulses at the output of the secondary of the transformer 70 to increase to 120 V.

Preferably, the voltage and/or current of the output signal 100 are monitored by a voltage sense circuit 92 and/or a current sense circuit 94. The output of these circuits 92, 94 is preferably fed back to the controller 40, and the controller 40 is preferably configured so that when and error condition is detected at the output 100 (e.g., overvoltage, overcurrent, severe voltage drop, etc.), the controller 40 will shut down the power switcher 60 by inhibiting the generation of both the first control signal and the second control signal that are applied to the control input 68 of the power switcher 60. Optionally, shut down of the power switcher 60 may also be triggered by an over-temperature condition at the load by including appropriate temperature sensors and routing a signal back from those temperature sensors to the controller 40.

Note that in the illustrated embodiment, a single controller 40 is used to implement all the control functions and sequencing functions described herein. But in alternative embodiments, a programmable controller 40 may be combined with a hardwired sequencer to perform those two functions, respectively.

In some embodiments, the output of the current sense circuit 94 and or the voltage sense circuit 92 is fed back to the controller 40. In these embodiments, the controller can adjust the voltage at the output of the DC-DC converter 50 by writing appropriate control words to the DAC 42 in order to adjust the current or voltage of the output signal 100 to a desired level. For example, when the controller 40 is set to adjust the current to a particular level and the output of the current sense circuit 94 indicate that the current is too low, the controller can increase the voltage at the output of the DAC 42, which will cause an increase in amplitude at the output signal 100. Similarly, if the output of the current sense circuit 94 indicate that the current is too high, the controller can decrease the voltage at the output of the DAC 42, which will cause a corresponding decrease in amplitude at the output signal 100.

In alternative embodiments, the transformer 70 (shown in FIGS. 1 and 2) can be omitted, in which case the two conductors at the output of the power switcher 60 are hooked up directly to the two conductors at the input of the output filter 80. In these embodiments, current flows directly from the output of the power switcher 60 to the input of the output filter 80 with no intervening transformer. But these alternative embodiments are less preferred, especially in situations when isolation is desirable and in situations where a high voltage output is desirable. In addition, these alternative embodiments cannot rely on the leakage inductance of the transformer to provide some or all of the inductance needed for the first stage of the filter.

Note that the design of the FIG. 1 embodiment relies on advance knowledge of the incoming signal, and the intentional construction of both the signal and the output filter 80 so that the most significant harmonics are either inherently zero (e.g., the even harmonics and the third harmonic) or zeroed out by the output filter 80 (e.g., the fifth and seventh harmonics). This helps provide a very clean high voltage output signal at the desired frequency, with very high efficiency.

The FIG. 1 embodiment uses a single DC-DC converter 50, and implements six equally-spaced sampling points per cycle. In alternative embodiments, the number of sampling points may be increased to N=2+4n, where n is a positive integer. When n=1, we have the situation described above in connection with FIG. 1. When n=2, we have the situation described below in connection with FIG. 5, which uses two DC-DC converters. Other embodiments may be implemented for n>2 following the same framework using additional DC-DC converters and even more samples (following the rule that N=2+4n).

Figure 5:
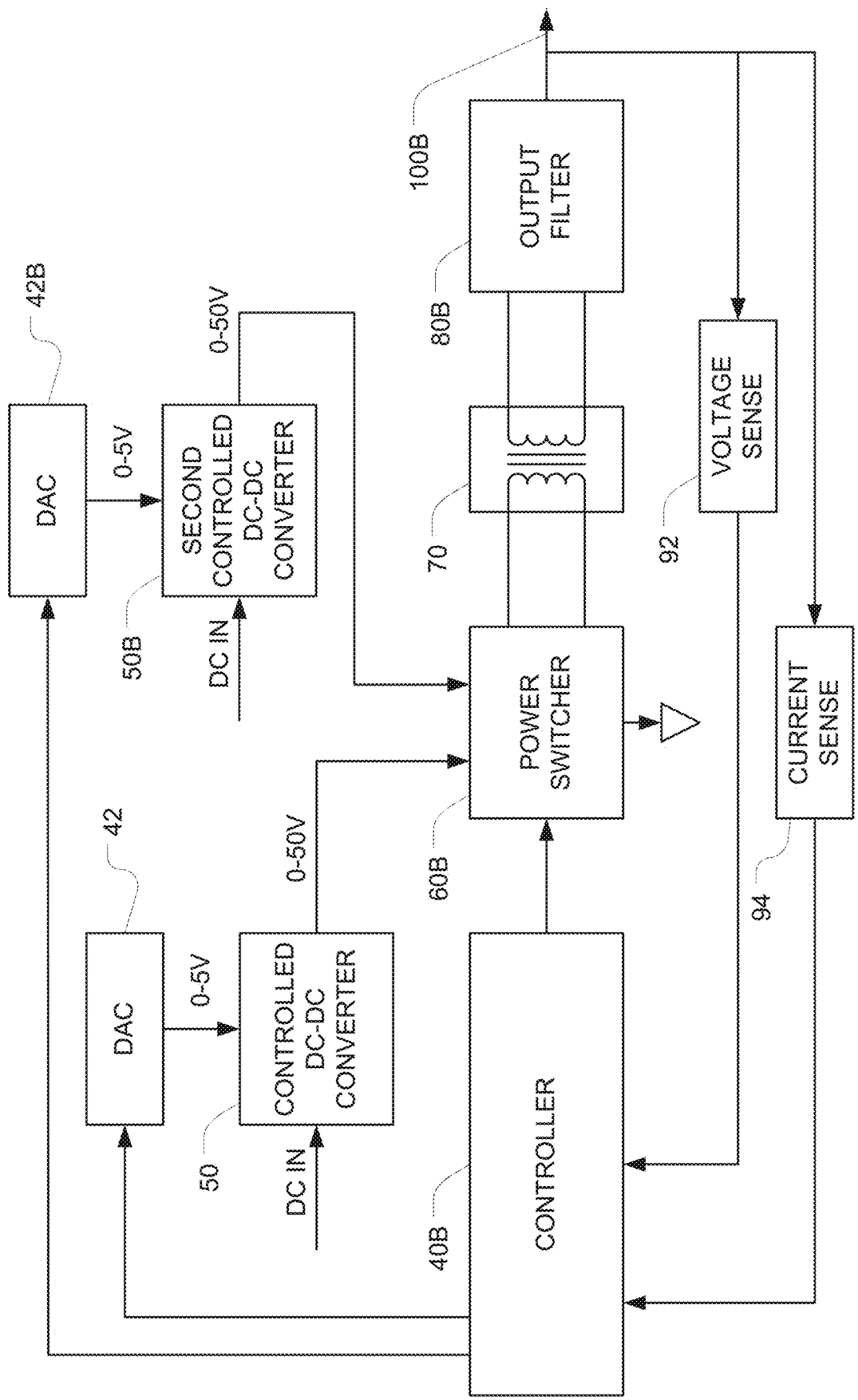
FIG. 5 is a block diagram of a second embodiment of a sinusoid generator that generates a sinusoid at a pre-set frequency f, with a controllable amplitude.

FIG. 5 is a block diagram of a second embodiment of a sinusoid generator that generates a sinusoid at a pre-set frequency f, with controllable amplitude, in which n=2. As a result, there are two DC-DC converters 50, 50B and (following the formula N=2+4n) 10 samples per cycle are used. Note that in the FIG. 5-6 embodiment, components with similar reference numbers operate in a manner similar to the description above in connection with the FIG. 1-2 embodiment.

Figure 7:
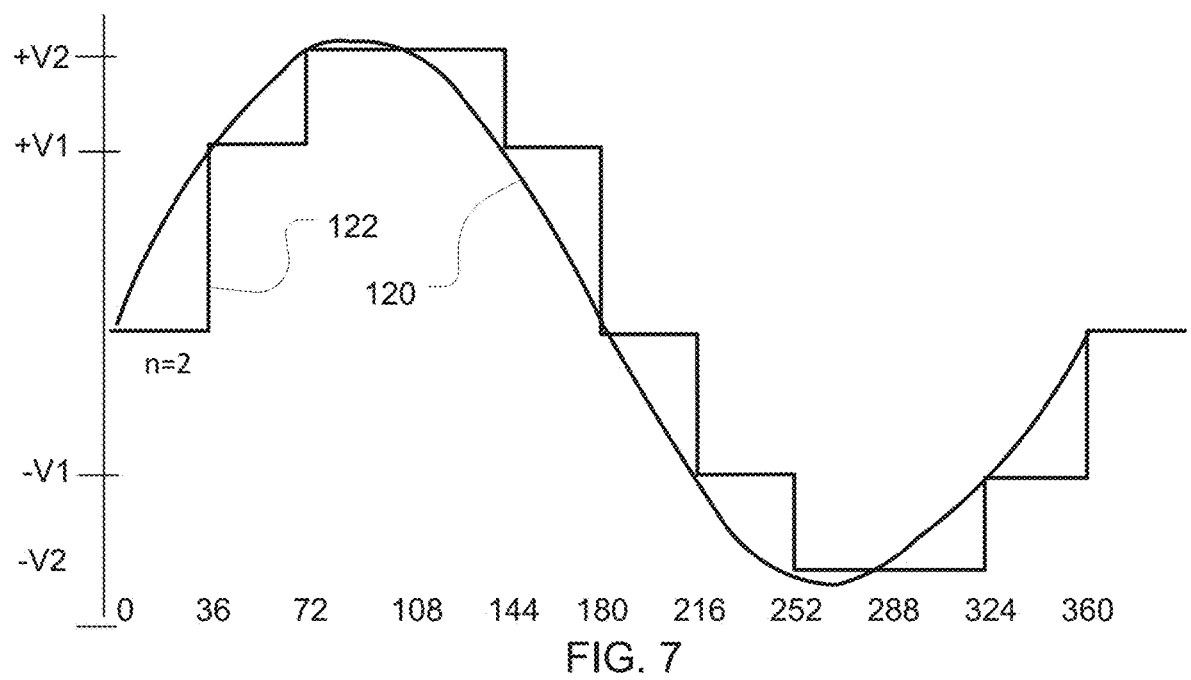
FIG. 7 depicts a sine wave and an oversampled version of that sine wave that is sampled 10 times per cycle.

FIG. 7 depicts a sine wave 120 and an oversampled version of that sine wave 122 that is sampled 10 times per cycle (i.e., at 0°, 36°, 72°, . . . 324°, and 360°. Looking at this oversampled version 112, it becomes apparent that it contains only five voltage levels: a low positive voltage +V1, a higher positive voltage +V2, a low negative voltage −V1, a higher negative voltage −V2, and zero volts (between 0° and 36° and also between 180° and 216°). Here again, the zero Volt level exists because we have chosen the sampling times such that one of the sampling points occurs at 0° and another one of the sampling points occurs at 180°, where the sine function equals zero. This choice advantageously reduces the number of voltage levels that must be generated to construct the oversampled version 122 of the sine wave to two levels (i.e., V1 and V2).

As a result, a controller 40B can be used to control the generation of an oversampled version of a sine wave that is sampled N times per cycle using evenly spaced samples that include a sampling point at 0°, where N=2+4n, by setting the output voltages of the DC power sources to levels that are present on the oversampled version of the sine wave, and then sequencing the control signal through the 2n states and the additional off state, so that each of the DC power sources is applied to the primary of the transformer in each direction at appropriate times in a sequence so as to generate the oversampled version of the sine wave.

When n=2 (as it is in the FIG. 5-6 embodiment), an oversampled version of a sinusoid at a pre-set frequency f can be constructed at the output of the transformer 70 by continuously repeating the following eight steps: applying V1 to the primary of the transformer 70 in the first direction between 36° and 72°; applying V2 in the first direction between 72° and 144°; applying V1 in the first direction between 144° and 180°; remaining off between 180° and 216°; applying V1 in the second direction between 216° and 252°; applying V2 in the second direction between 252° and 324°; applying V1 in the second direction between 324° and 360°; and remaining off between 0° and 36°. Note that in order for the resulting waveform to properly track an oversampled version of a sinusoid (122 in FIG. 7), the ratio between V1 and V2 must remain constant. More specifically, the ratio V2/V1 must equal sin(72°)/sin(36°, which comes to 1.618.

The controller 40B is responsible for generating control signals that cause the power switcher 60B to apply these voltages to the transformer 70 in the sequence identified above. The controller 40B is similar to the controller 40 in the FIG. 1 embodiment, except that it sequences through 10 states per cycle instead of six states per cycle.

Figure 6:
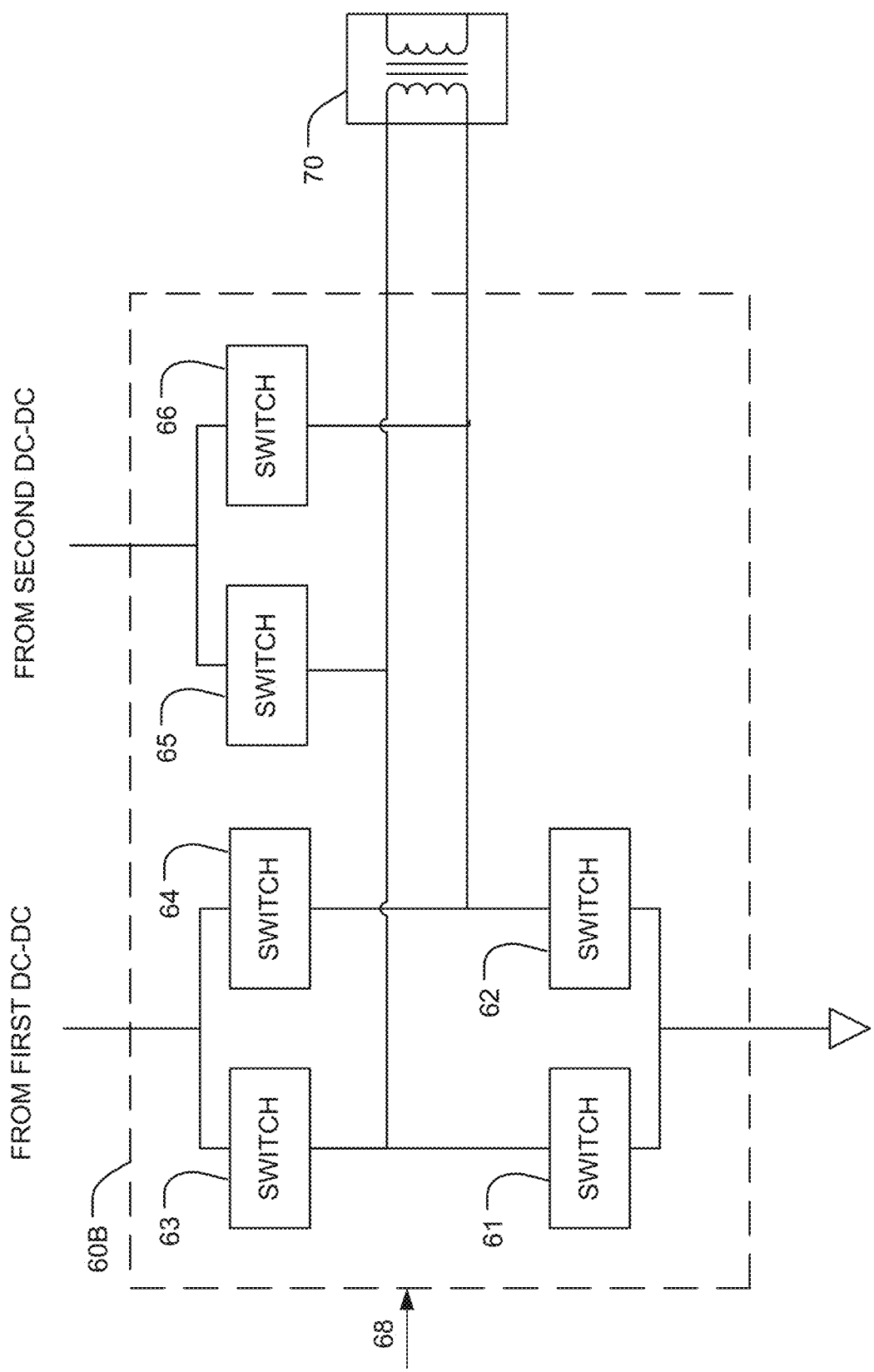
FIG. 6 is a block diagram of one preferred approach for implementing the power switcher in the FIG. 5 embodiment.

Referring now to FIG. 6, the power switch 60B has a control input 68, and the power switch is configured to either (a) apply the output of a selected one of the DC power sources to the primary of the transformer 70 in a selected direction in response to 2n states of a control signal that is applied to the control input 68 or (b) remain off in response to an additional state of the control signal.

FIG. 6 is a block diagram of one preferred approach for implementing the power switcher 60B. This power switcher is similar to the power switcher 60 of the FIG. 1 embodiment, except that it contains additional switches 65-66 for switching the output of the second DC-DC converter across the transformer 70 in either direction. More specifically, this power switcher 60B uses a set of six electronically controlled switches 61-66 connected to the primary of the transformer 70 as depicted in FIG. 6. These switches 61-66 (which are similar to the corresponding switches in the FIG. 1-2 embodiment) open and close in response to signals that are applied to a control input 68. In order to route the output of the first DC-DC converter 50 to the primary of the transformer 70 in the first direction, only switches 63 and 62 should be closed. In order to route the output of the first DC-DC converter 50 to the primary of the transformer 70 in the opposite direction (i.e., with an opposite polarity), only switches 61 and 64 should be closed. In order to route the output of the second DC-DC converter 50B to the primary of the transformer 70 in the first direction, only switches 65 and 62 should be closed. In order to route the output of the second DC-DC converter 50B to the primary of the transformer 70 in the opposite direction (i.e., with an opposite polarity), only switches 61 and 66 should be closed. When all six of these switches 61-66 are off, no power is routed into the primary of the transformer 70.

Returning to FIG. 5, an output filter 80B is connected to the secondary of the transformer 70, and the output filter passes the pre-set frequency f and attenuates frequencies above a cut-off frequency. The output filter 80B is similar to the output filter 80 in the FIG. 1-2 embodiment, except the location of the zeros in the transfer function of the output filter 80B must be adjusted to account for the different frequency content of the oversampled waveform 122 (shown in FIG. 7). More specifically, the output filter 80B should have a transfer function with a zero at a frequency where a harmonic of the pre-set frequency f is expected to contain power.

For example, because the waveform 122 has 10 samples per cycle, the initial harmonic that we would expect to appear will be the ninth harmonic. Accordingly, a transfer function with a zero at the ninth harmonic would be useful when this waveform 122 is being used. The cut off frequency of the filter should also be adjusted accordingly, based on the set of harmonics that are expected to appear (which can be calculated in advance by taking the Fourier transform of the waveform that is being used).

Optionally, the transfer function of the output filter 80B can also be designed to have a zero at the next frequency where a harmonic of the pre-set frequency f is expected to contain power. In the case of the waveform 122, this would be the eleventh harmonic.

The controller 40B controls an amplitude of the sinusoid at the output 100B of the output filter 80B by adjusting the output voltages of the DC power sources 50, 50B via their voltage-control inputs, while maintaining a fixed ratio between the output voltages of each of the DC power sources. In the illustrated embodiment, this is accomplished by writing appropriate control words to DAC 42 and DAC 42B, taking care to maintain the required ratio of sin(72°)/sin(36°) as described above. In alternative embodiments, the second DAC 42B can be eliminated, and replaced by a 1.618x hardware multiplier that is inserted between the output of DAC 42 and the voltage control input to the second DC-DC converter 50B.

In alternative embodiments, the transformer 70 can be omitted from the FIG. 5 embodiment, in which case the two conductors at the output of the power switcher 60B are hooked up directly to the two conductors at the input of the output filter 80B. In these embodiments, current flows directly from the output of the power switcher 60B to the input of the output filter 80B with no intervening transformer. But these embodiments are less preferred for the same reasons discussed above in connection with FIG. 1.

Note that the system descried above is suitable for generating high voltage signals of any shape, as long as the pulse train that will result in these signals can be determined before use either through calculations or experiments, and the filters are designed accordingly.

When the output signal generated by the system is applied to electrodes to generate TTFields (as described in U.S. Pat. No. 7,805,201) changes in the load associated with the body of the patient and the transducer arrays can change the output signal due to interactions with the output filter. This means that any changes to this load (e.g., lifting of a disk off a patient's body, short circuiting etc.) immediately influence the output signal, which is constantly monitored. Hence, it is possible for the device to respond very quickly to these changes (e.g., by shutting down the power switcher 60 in response to the detection of a short circuit or overload condition).

Notably, in the embodiments described above, the exact shape of the desired output signal is known in advance at every moment because we are generating a sine wave at a known frequency. It is only the amplitude of the output signal that changes over time based on the controller responding to external inputs (e.g., current measurements or temperature measurements). The embodiments described above can advantageously be used to generate very clean narrow band limited signals in the frequency range of 100-500 kHz, with very low losses and very low sensitivity to the external load to which the signal generator is connected.

In alternative embodiments, the system can be used to generate a sinusoid at any desired frequency within a pre-set range by building the filter using a component with a tunable reactance (e.g. a tunable capacitance or a tunable inductance). In these embodiments, the reactance of the tunable components is set to imbue the filter with the desired transfer function characteristics. Then, an appropriate oversampled sinusoid is generated and fed into the filter as discussed above in connection with FIGS. 1 and 5.

In other alternative embodiments, the system can be used to generate a finite number of pre-defined signals at a plurality of different pre-set frequencies. These embodiments can be implemented by saving the characteristics of the pulse trains for each of the pre-defined signals in a look up table, and providing a bank of filters that can be selectively switched in to the signal path so as to provide the filtering characteristics necessary to generate the desired one of the pre-defined signals. When using the system to generate one of the pre-defined signals, the characteristics of the required pulse train are retrieved from memory and the appropriate filter (i.e., the one that matches this pulse train) is switched in to the signal path.

In other alternative embodiments, composite signals that contain a small number of discrete frequencies (e.g., between two and five frequencies) can be generated by generating an oversampled version of the composite signal, and passing the oversampled version of the composite signal through an appropriate filter.

In the FIG. 1 and FIG. 5 embodiments described above, depending on the construction of the DC-DC converters 50/50B, the possibility exists that high-frequency artifacts (e.g., spikes) may appear on the output 100/100B when the output voltage of those DC-DC converters changes (e.g., when the controller 40/40B writes a new control word to the DAC 42/42B). And because high-frequency artifacts can create an unpleasant sensation in the person being treated with TTFields therapy, it is preferable to take steps to prevent such high-frequency artifacts.

One suitable approach that prevents high-frequency artifacts from appearing on the output 100/100B is to deliberately slow down the response time of the DC-DC converters 50/50B (e.g., by adding a sufficiently large capacitor across the output of each DC-DC converter). But while this approach is effective, it has two drawbacks: first, additional components must be included in the circuit. And second, slowing down the response time of the system will prevent the output voltage from changing rapidly in situations when rapid changes may be desirable.

Figure 8:
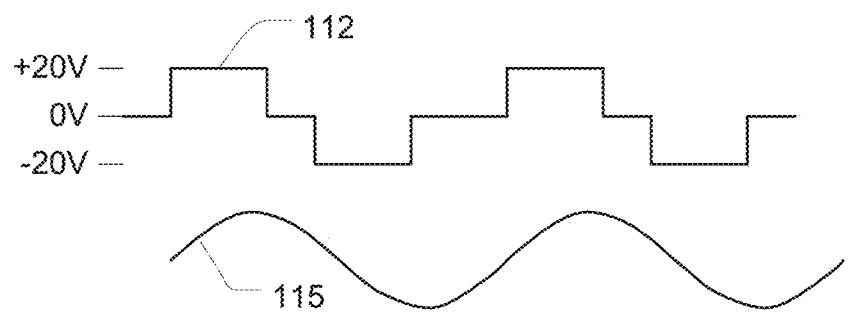
FIG. 8 depicts a sinusoidal output waveform under steady-state conditions
Figure 9:
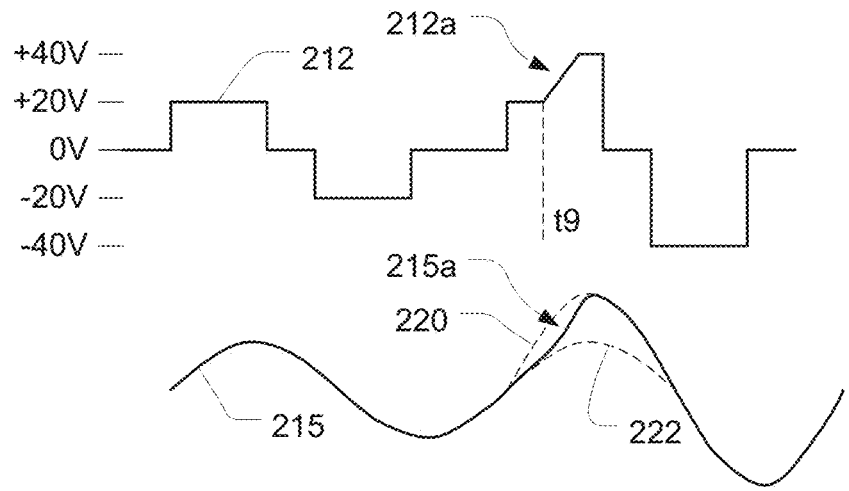
FIG. 9 shows how the sinusoidal output waveform changes when the output of the DC-DC converter being used to power the sinusoidal output changes at certain times in the cycle.
Figure 10:
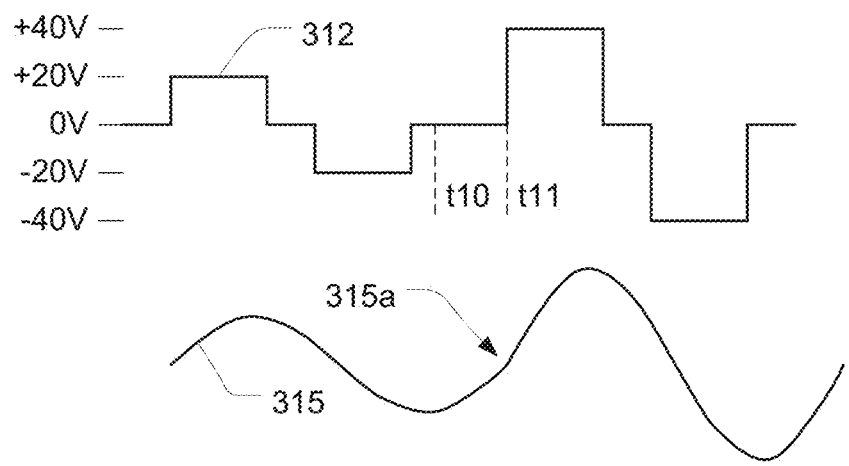
FIG. 10 shows how the sinusoidal output waveform changes when the output of the DC-DC converter being used to power the sinusoidal output changes at other times in the cycle.

FIGS. 8-10 depict an alternative approach for preventing high-frequency artifacts from appearing on the output 100/100B without deliberately slowing down the response time of the DC-DC converters 50/50B.

More specifically, FIG. 8 depicts the same waveform 112 described above in connection with FIG. 3 (which appears at the output of the power switcher 60 in FIG. 1) and the sinusoidal output waveform 115 (which appears at the output 100 of the output filter 80 in FIG. 1) under steady-state conditions (e.g., when the voltage at the output of the DC-DC converter 50 in FIG. 1 is held at a constant 20 VDC, which means that the controller 40 in FIG. 1 is not updating the contents of the DAC 42). In this steady-state situation, the output waveform 115 will operate as described above in connection with FIGS. 1-4, and will not include any high frequency artifacts.

FIG. 9 shows how things change when a DC-DC converter with a rapid response time is used, and the output of the DC-DC converter 50 (shown in FIG. 1) changes from 20 VDC to 40 VDC. As explained above in connection with FIG. 1, the controller 40 could initiate this change by updating the contents of the DAC 42 at time t9. Prior to this time t9, the output waveform 215 will be identical to the output waveform 115 in the FIG. 8 example. But as soon as the controller 40 updates the contents of the DAC 42 at time t9, because the output of the DAC 42 is applied to the voltage-control input of the DC-DC converter 50, the output voltage of the DC-DC converter will rapidly begin to change (e.g., from 20 V to 40 V in the illustrated example). And because the power switch 60 is set to actively source current from the DC-DC converter 50 into the transformer 70 at that instant t9, the rapid change in current will travel through the transformer 70 and into the output filter 80, which will add a high-frequency artifact 215 to the output 100. (Note that the dashed line 222 represents a continuation of the original sinusoid that existed prior to t9, and the dashed line 220 represents a clean sinusoid at twice the original amplitude.)

A similar situation exists when the design of the DC-DC converter is such that spikes and/or instabilities can appear on the output of the DC-DC converter in response to changes on the DC-DC converter's voltage-control input (regardless of the response time of the DC-DC converter). More specifically, if the power switch 60 is set to actively source current from the DC-DC converter 50 into the transformer 70 at the instant the voltage-control input of the DC-DC converter changes, any spikes on the output of the DC-DC converter will travel through the transformer 70 and into the output filter 80, which will add high-frequency artifacts 215 to the output 100.

Under certain circumstances, high-frequency artifacts could be added to the output 100 if the output voltage of the DC-DC converter changes during an interval of time when the power switch 60 is set to actively source current from a DC-DC converter 50/50B into the transformer 70. If, on the other hand, the output of the DC-DC converter is changed during an interval of time when the power switch 60 is not actively sourcing current from a DC-DC converter 50/50B into the transformer 70, high-frequency artifacts will not appear at the output 100. The controller 40/40B in the FIG. 1/5 embodiments can take advantage of this dichotomy to prevent high-frequency artifacts from appearing on the output 100/100B. More specifically, the controller 40/40B does this by ensuring that the output of the DC-DC converter 50/50B is only changed during intervals when the power switcher 60/60B is not actively sourcing current from a DC-DC converter.

In the context of the FIG. 1 embodiment described above, the controller 40 accomplishes this by preventing adjustments of the voltage-control input of the DC-DC converter 50 from occurring when either (a) the first control signal is being applied to the control input of the power switcher 60 (i.e., when the power switcher 60 is routing the output of the DC-DC converter 50 to the primary of the transformer 70 in one direction) or (b) the second control signal is being applied to the control input of the power switcher 60 (i.e., when the power switcher 60 is routing the output of the DC-DC converter 50 to the primary of the transformer 70 in the opposite direction). When neither the first control signal nor the second control signal is being applied to the control input, the power switcher 60 will remain off, in which case the controller 40 can make adjustments to the voltage-control input of the DC-DC converter 50 without introducing a high-frequency artifact on the output 100.

FIG. 10 shows how things unfold in the context of the FIG. 1 embodiment when the output of the DC-DC converter 50 changes from 20 VDC to 40 VDC during a time t10 when the power switch 60 is not actively sourcing current from the DC-DC converter. Prior to this time t10, the output of the DC-DC converter 50 will be at a first level (e.g., 20 V in the illustrated example), and the output waveform 315 will be identical to the output waveform 115 in the FIG. 8 example. The controller 40 updates the contents of the DAC 42 at time t10, when the power switch 60 is not actively sourcing current from the DC-DC converter 50 into the transformer 70. The output voltage of the DC-DC converter 50 will rapidly begin to change (e.g., from 20 V to 40 V in the illustrated example) and will stabilize before the power switch 60 begins to route current into the transformer 70 at t11. Because the output of the DC-DC converter 50 has already stabilized when the power switch 60 begins to route current into the transformer 70 at t11, the waveform that will enter the output filter after t11 will be an oversampled sine wave with a different amplitude (e.g., 40 V). And as explained above in connection with FIGS. 1-4, when an oversampled sine wave is provided to the output filter 80, the resulting output 100 will be a very clean sinusoid.

Similarly, in the context of the FIG. 5 embodiment described above, the controller 40B prevents high-frequency artifacts from appearing on the output 100B by ensuring that the output of any given DC-DC converter 50/50B is only changed during intervals when the power switch 60 is not actively sourcing current from the given DC-DC converter. The controller 40B accomplishes this by not adjusting the output voltage of any DC power source while its output is being routed to the output terminals of the power switcher 60.

Figure 11:
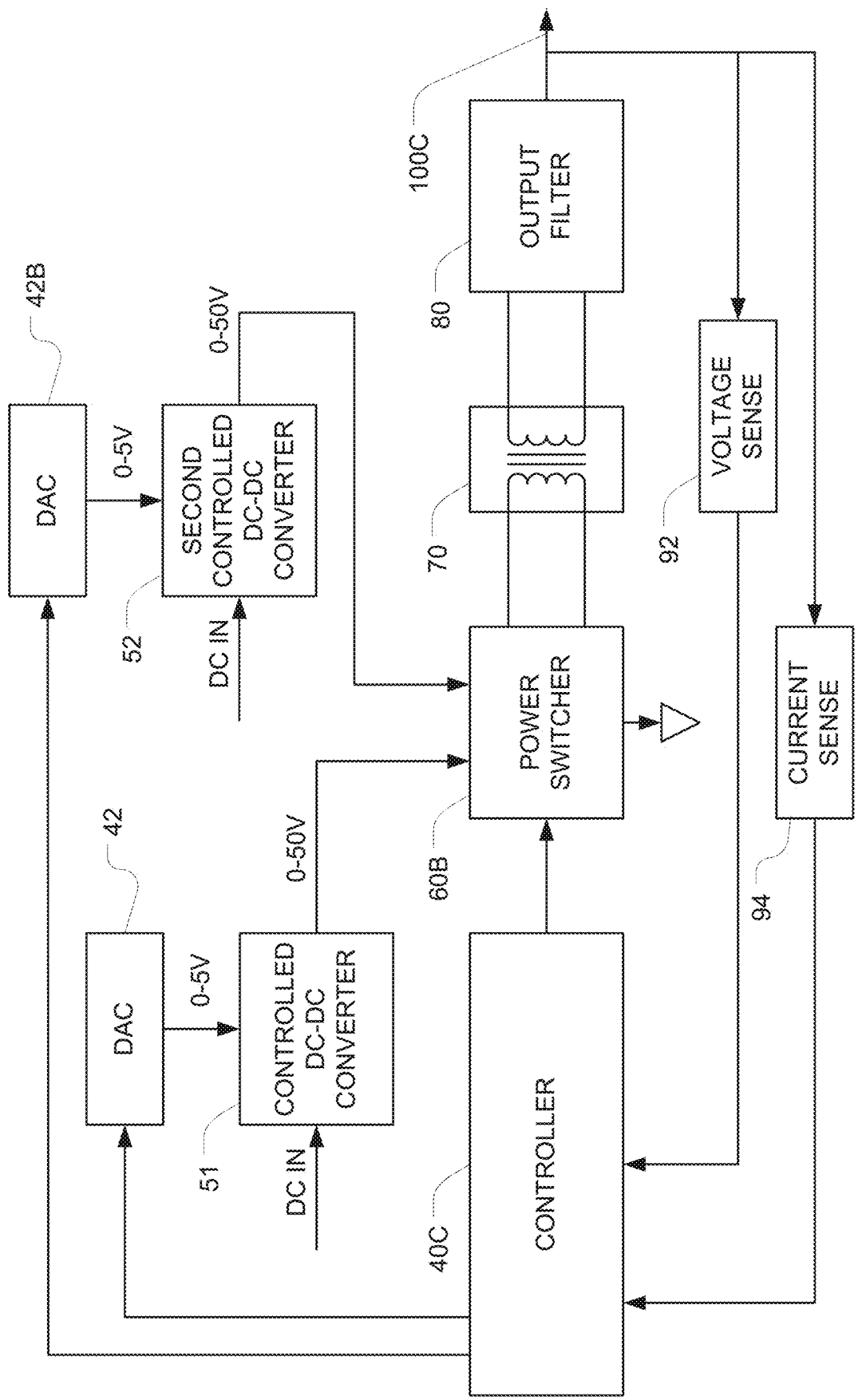
FIG. 11 is a block diagram of a third embodiment of a sinusoid generator that generates a sinusoid with a controllable amplitude.

FIG. 11 is a block diagram of a third embodiment of a sinusoid generator that generates a sinusoid at a pre-set frequency f, with controllable amplitude. Components with similar reference numbers operate in a manner similar to the corresponding components described above in connection with FIGS. 1-5.

This embodiment uses two DC-DC converters 51, 52. Each of these DC-DC converters is configured to multiply an analog voltage-control input signal by a fixed number (e.g., 10). In this example, when a 1 V voltage-control signal is applied the output will be 10 V, and when a 5 V voltage-control signal is applied the output will be 50 V, with proportional control therebetween. The output of the DC-DC converters 51, 52 can therefore take any value between 0 and 50 V, depending on the voltage (e.g., 0-5 V) that is applied to the analog voltage-control input. The controller 40C controls the output voltage of the DC-DC converters 51, 52 by writing control words to the DACs 42, 42B. The DACs then generate analog voltages that are proportional to the control words, and these analog voltages are applied to the voltage-control inputs of the DC-DC converters 51, 52.

The controller 40C is responsible for generating control signals that cause the power switcher 60B to apply these voltages to the transformer 70 in the sequence described below.

FIG. 6 is a block diagram of one preferred approach for implementing the power switcher 60B. This power switcher is identical to the power switcher 60B of the FIG. 5 embodiment. More specifically, this power switcher 60B uses a set of six electronically controlled switches 61-66 connected to the primary of the transformer 70 as depicted in FIG. 6. These switches 61-66 open and close in response to signals that are applied to a control input 68.

In order to route the output of the first DC-DC converter 51 to the primary of the transformer 70 in the first direction, only switches 63 and 62 should be closed. The power switcher 60B is configured so that this occurs in response to a first state of the control input. In order to route the output of the first DC-DC converter 51 to the primary of the transformer 70 in the opposite direction (i.e., with an opposite polarity), only switches 61 and 64 should be closed. The power switcher 60B is configured so that this occurs in response to a second state of the control input.

In order to route the output of the second DC-DC converter 52 to the primary of the transformer 70 in the first direction, only switches 65 and 62 should be closed. The power switcher 60B is configured so that this occurs in response to a third state of the control input. In order to route the output of the second DC-DC converter 52 to the primary of the transformer 70 in the opposite direction (i.e., with an opposite polarity), only switches 61 and 66 should be closed. The power switcher 60B is configured so that this occurs in response to a fourth state of the control input. When all six of these switches 61-66 are off, no power is routed into the primary of the transformer 70. The power switcher 60B is configured so that this occurs in response to a fifth state of the control input (also referred to herein as an additional state).

The controller 40C has the ability to operate in either a first mode or a second mode. In the first mode, the controller 40C generates an output waveform 100C powered exclusively from the first DC-DC converter 51 by setting the control input of the power switcher 60B to the first and second states in an alternating sequence while holding the first voltage-control input constant. In some preferred embodiments, a waveform similar to the waveform 112 in FIG. 3 can be generated by (a) placing the control input in the first state for a duration of T/3, then (b) waiting for a duration of T/6, then (c) placing the control input in the second state for a duration of T/3, and then (d) waiting for a duration of T/6, then continuously repeating the sequence (a), (b), (c), and (d). The amplitude of this waveform will depend only on the output voltage of the DC-DC converter 51. Filtering of this waveform by the output filter 80 (which is identical to the output filter 80 in the FIG. 1-2 embodiment) will result in a clean sinusoid (as explained above in connection with FIGS. 1-4).

In the second mode, the controller 40C generates an output waveform 100C powered exclusively from the second DC-DC converter 52 by setting the control input of the power switcher 60B to the third and fourth states in an alternating sequence while holding the second voltage-control input constant. In some preferred embodiments, a waveform similar to the waveform 112 in FIG. 3 can be generated by (e) placing the control input in the third state for a duration of T/3, then (f) waiting for a duration of T/6, then (g) placing the control input in the fourth state for a duration of T/3, and then (h) waiting for a duration of T/6, then continuously repeating the sequence (e), (f), (g), and (h). The amplitude of this waveform will depend only on the output voltage of the DC-DC converter 52. Filtering of this waveform by the output filter 80 will result in a clean sinusoid.

Figure 12:
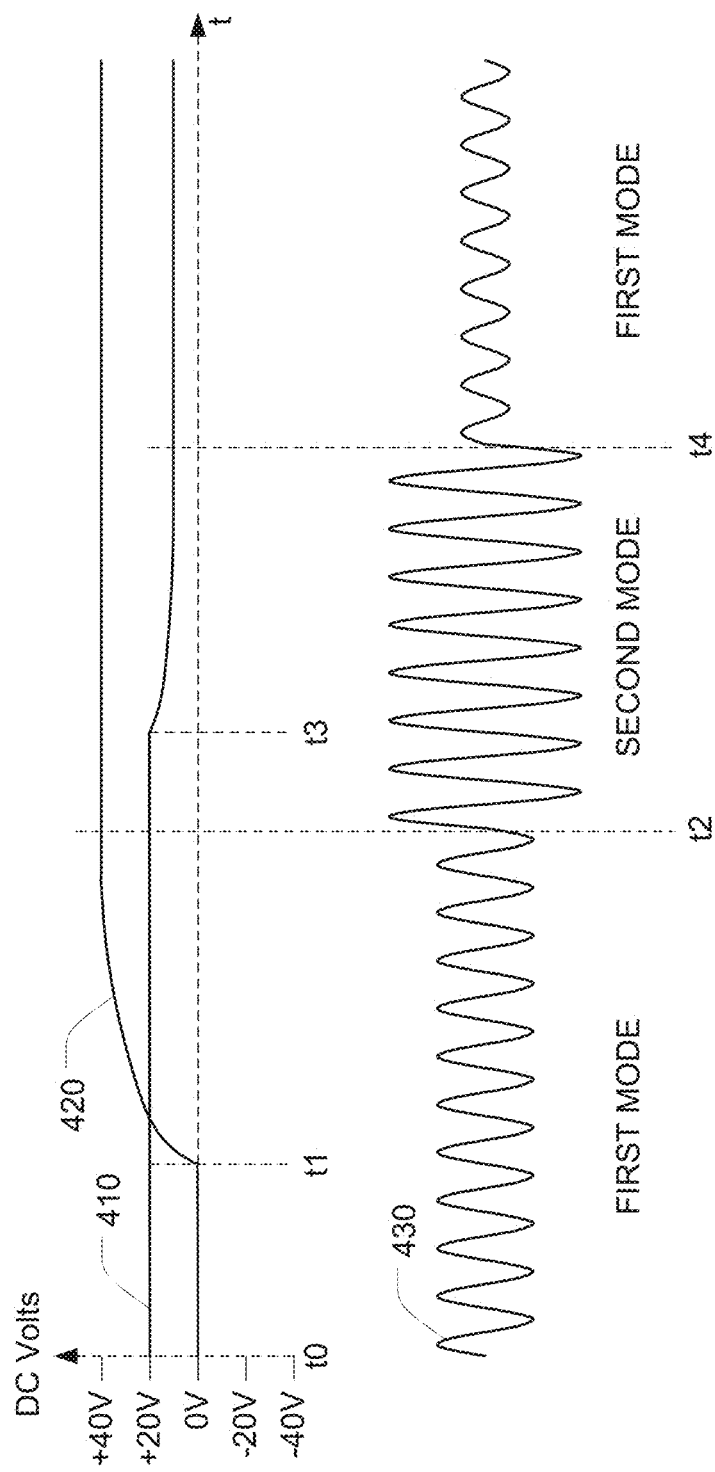
FIG. 12 depicts waveforms showing how the FIG. 11 embodiment facilitates rapid changes to the voltage of the output signal.

FIG. 12 illustrates how the FIG. 11 embodiment facilitates rapid changes to the voltage of the output signal 100C by switching between the first and second modes. Trace 410 is the output voltage of the first DC-DC converter 51, trace 420 is the output voltage of the second DC-DC converter 52, and trace 430 is the output signal. FIG. 11 begins at t0, with the controller 40C operating in the first mode. In this mode, the output waveform 430 is powered exclusively from the first DC-DC converter 51 (which is set to 20 V in the illustrated example). The controller 40C controls generation of the output waveform 430 by setting the control input of the power switcher 60B to the first and second states in an alternating sequence (with wait times interspersed at appropriate times) while holding the first voltage-control input constant, as described above.

While still operating in the first mode, the controller 40C determines in advance what the output voltage will be when it eventually switches into the second mode. The controller 40C then issues a command at time t1, which causes the output voltage of the second DC-DC converter 52 to move to the desired level. In the illustrated example, the desired level for the second DC-DC converter 52 is 40 V. Notably, the reaction time of the second DC-DC converter can be very slow because the second DC-DC converter is not being used at this time.

Preferably after the output of the second DC-DC converter 52 has settled to the desired level, the controller 40C switches into the second mode. This transition from the first mode to the second mode occurs at a time when the power switcher 60B is in the fifth state and is not routing current to the transformer 70. In the second mode, the output waveform 430 is powered exclusively from the second DC-DC converter 52 (which is set to 40 V in the illustrated example). The controller 40C controls generation of the output waveform 430 by setting the control input of the power switcher 60B to the third and fourth states in an alternating sequence (with wait times interspersed at appropriate times) while holding the second voltage-control input constant, as described above. Preferably, the command that initiates the change in voltage of the second DC-DC converter 52 (i.e., t1 in FIG. 12) occurs far enough in advance (e.g., at least 1 ms) before the controller 40C switches into the second mode (i.e., t2 in FIG. 12) to allow the output of the second DC-DC converter 52 to settle at the desired level, so that when the second mode begins at t2 the output waveform 430 will immediately go to the desired level.

A similar process occurs when transitioning from the second mode back to the first mode. More specifically, while still operating in the second mode, the controller 40C determines in advance what the output voltage will be when it eventually switches into the first mode. The controller 40C then issues a command at time t3, which causes the output voltage of the first DC-DC converter 52 to move to the desired level. In the illustrated example, the new desired level for the first DC-DC converter 51 is 10 V. Notably, the reaction time of the first DC-DC converter can be very slow because the first DC-DC converter is not being used at this time.

Preferably after the output of the first DC-DC converter 51 has settled to the desired level, the controller 40C switches into the first mode. This transition from the second mode to the first mode occurs at a time when the power switcher 60B is in the fifth state and is not routing current to the transformer 70. In the first mode, the output waveform 430 is powered exclusively from the first DC-DC converter 51 (which is set to 10 V in the illustrated example). The controller 40C controls generation of the output waveform 430 by setting the control input of the power switcher 60B to the first and second states in an alternating sequence (with wait times interspersed at appropriate times) while holding the first voltage-control input constant, as described above. Preferably, the command that initiates the change in voltage of the first DC-DC converter 51 (i.e., t3 in FIG. 12) occurs far enough in advance (e.g., at least 1 ms) before the controller 40C switches into the first mode (i.e., t4 in FIG. 12) to allow the output of the first DC-DC converter 51 to settle at the desired level, so that when the first mode begins at t4 the output waveform 430 will immediately go to the desired level.

In alternative embodiments, the transformer 70 can be omitted from the FIG. 11 embodiment, in which case the two conductors at the output of the power switcher 60B are hooked up directly to the two conductors at the input of the output filter 80. In these embodiments, current flows directly from the output of the power switcher 60B to the input of the output filter 80 with no intervening transformer. But these embodiments are less preferred for the same reasons discussed above in connection with FIG. 1.

TTFields therapy involves inducing an electric field (e.g., at 200 kHz) through a target body part in order to treat a tumor in that body part. Experiments have shown that the efficacy of TTFields increases when the direction of the TTFields changes during the course of treatment. For example, in the Optune® prior art system, the direction of the TTFields changes every 1 s. But in alternative embodiments, the direction can change at a different rate (e.g., between 50 ms and 10 s).

Figure 13:
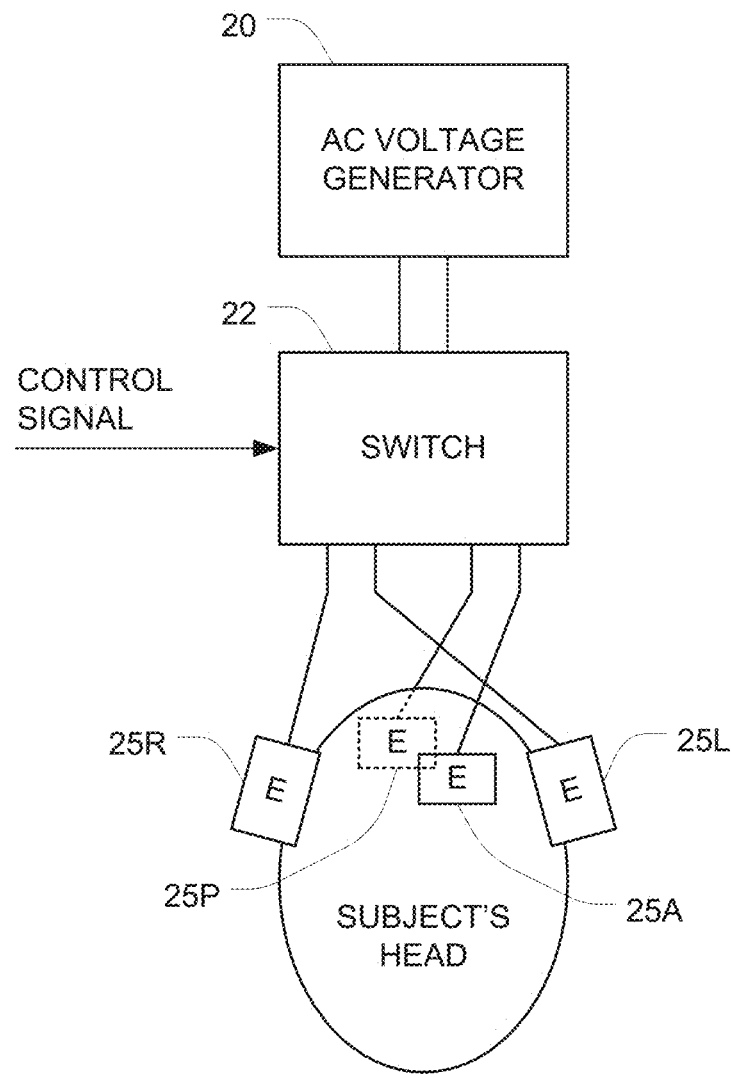
FIG. 13 is a block diagram of a prior art system for applying TTFields to a person's head.

FIG. 13 is a block diagram of the original Optune® prior art system for applying TTFields to a person's head (or other body part) in two different directions. This is accomplished using one pair of transducer arrays 25A, 25P positioned on the front and back of the head (i.e., anterior and posterior) and another pair of transducer arrays 25L, 25R positioned on the left and right sides of the person's head. More specifically, when an AC voltage is applied between transducer arrays 25L and 25R, an electric field that primarily runs in a left-to-right (LR) direction will be induced in the subject's head. And when an AC voltage is applied between transducer arrays 25A and 25P, an electric field that primarily runs in a anterior-to-posterior (AP) direction will be induced in the subject's head. TTFields may also be applied to other parts of the body (e.g., pancreas, lungs, etc.) by positioning transducer arrays of the subject' skin in front/back of the relevant body part and right/left of the relevant body part.

In the FIG. 13 embodiment, a single AC voltage generator 20 is used to drive both transducer array pairs (i.e., 25L/R and 25A/P). This is accomplished by routing the output of the AC voltage generator 20 into a switch 22. Depending on the state of the control signal, the switch 22 will either route the signal from the AC voltage generator 20 across one pair of transducer arrays (i.e. 25L/R) or the other pair of transducer arrays (i.e. 25A/P).

FIG. 14 is a timing diagram that shows the sequencing between the two directions LR and AP that was used in the original Optune®. In this approach, the switch 22 would (a) route the output of the AC voltage generator 20 to the left and right transducer arrays (25L/R) for one second, then (b) route the output of the AC voltage generator 20 to the anterior and posterior transducer arrays (25A/P) for one second, and then repeat steps (a) and (b) in an alternating sequence. A short duration of time (e.g., 5-10 ms) during which the output of the AC voltage generator 20 was not routed to either pair of transducer arrays (25L/R, 25A/P) was interposed between each step (indicated by the label OFF).

Figure 16A:
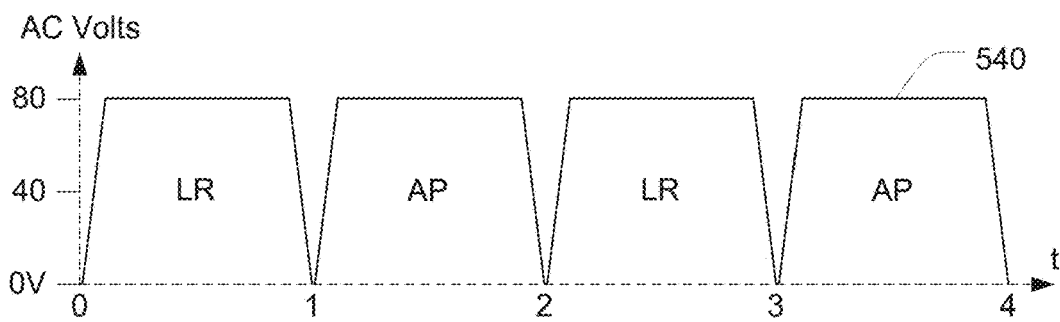
FIG. 16A depicts a prior art approach for avoiding the FIG. 15 spike by ramping the output voltage of the AC generator up and down, with a 1 s interval between switching events.

One issue that was addressed during the design of the original Optune® is explained in connection with FIG. 15. More specifically, if the switch 22 switched from the OFF state to either the LR state or the AP state (trace 525) while the instantaneous output voltage 520 generated by the AC voltage generator 20 was substantial (e.g., >10 V), the output waveform would resemble trace 530, which includes a spike 532. Because such a spike 532 could cause the subject to experience an uncomfortable sensation, the original Optune® was designed to prevent such spikes from occurring. More specifically, this was accomplished by ramping down the output voltage of the AC voltage generator 20 from its steady-state value to zero V during the 100 ms interval that preceded each OFF state, then ramping the output voltage back up to its steady-state value during the 100 ms interval that followed each OFF state, as depicted in FIG. 16A, trace 540. The ramp rate was about 1 V/ms, which was sufficiently slow to avoid spikes that might be noticeable to a patient.

Figure 16B:
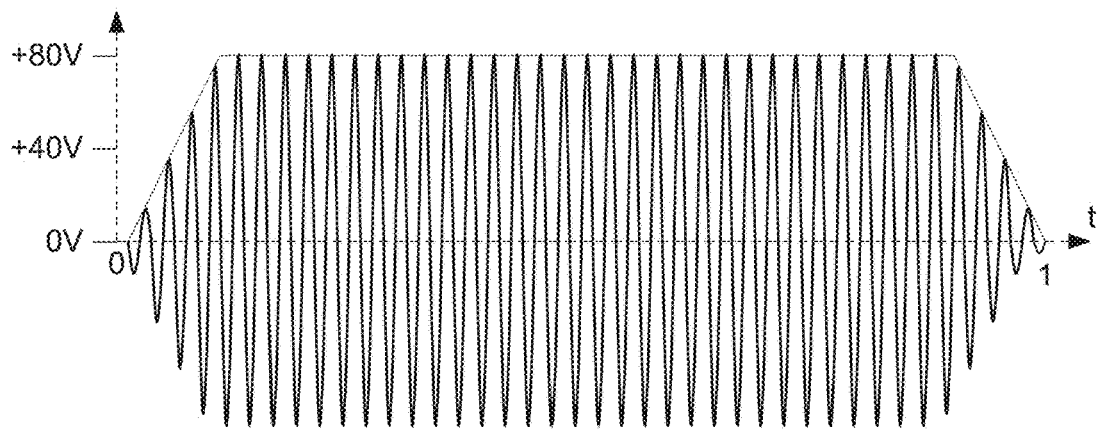
FIG. 16B is a schematic representation of the instantaneous output voltage of the AC generator using the ramp rate depicted in FIG. 16A.

The resulting waveform at the output of the AC voltage generator 20 resembled the waveform depicted in FIG. 16B (except that the actual frequency of the sinusoid generated by the AC voltage generator 20 would be orders of magnitude higher than the depicted sinusoid). Note that the scale of the x-axis in FIG. 16B is magnified 4× with respect to FIG. 16A, in order to show additional detail. And this solution worked quite well in the context of the original Optune®, because the system operated at its peak output voltage 80% of the time, and only 20% of the time was spent either ramping up the voltage, ramping down the voltage, or with the voltage switched off.

Figure 17A:
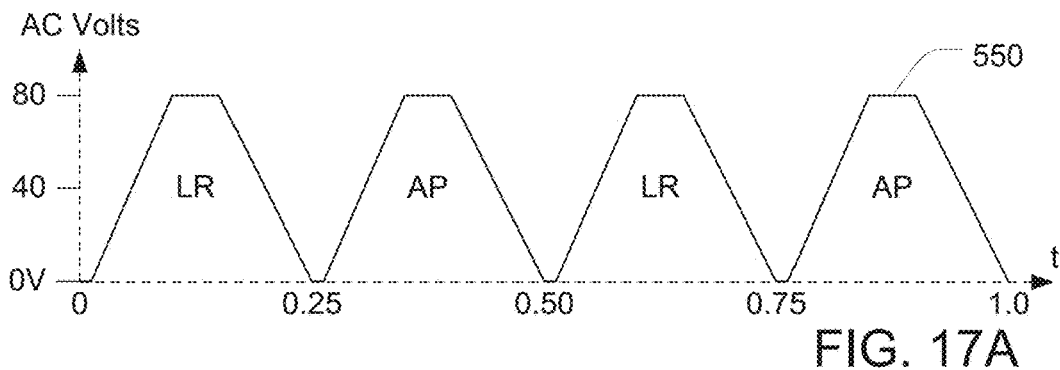
FIG. 17A depicts what would happen if the FIG. 16 approach is used with a 0.25 s interval between switching events.
Figure 17B:
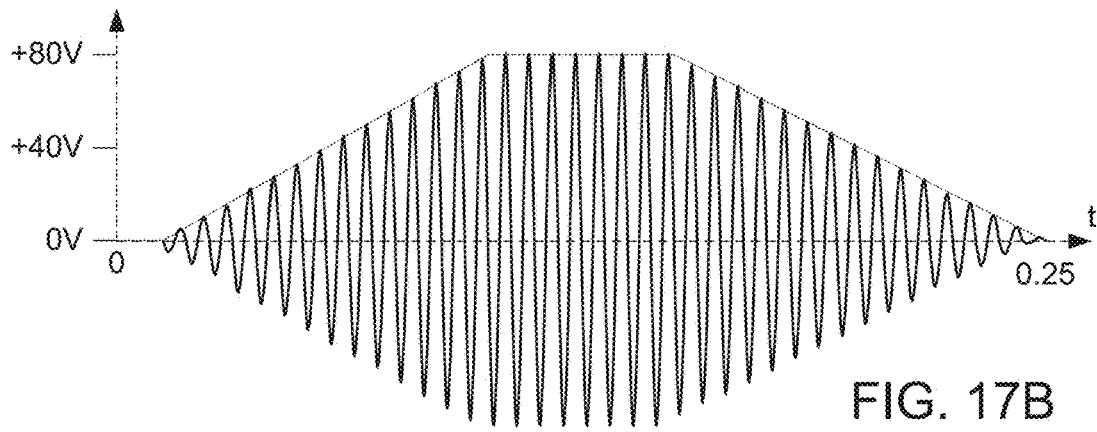
FIG. 17B is a schematic representation of the instantaneous output voltage of the AC generator using the ramp rate depicted in FIG. 17A.

Let us now examine what would happen if a similar approach is used, but the interval that the AC voltage is applied to either the LR or AP transducer arrays is reduced from 1 s to 0.25 s. If the same 1 V/ms ramp-down and ramp-up approach described above in connection with FIG. 16A is used at this new timescale, the output voltage of the AC voltage generator 20 would follow trace 550 in FIG. 17A. And as a result, the waveform at the output of the AC voltage generator 20 would resemble the waveform depicted in FIG. 17B (except that, once again, the actual frequency of the sinusoid generated by the AC voltage generator 20 would be orders of magnitude higher than the depicted sinusoid). Note that the scale of the x-axis in FIG. 17B is magnified 4× with respect to FIG. 17A, in order to show additional detail.

But this solution is less than ideal because the peak output voltage would only be applied to the transducer arrays 20% of the time, which means that the maximum electric field would only be applied to the subject 20% of the time. Thus, unlike the prior art situation depicted in FIGS. 16A/B (in which the output voltage was ramped up/down to ensure patient comfort, and the ramping only reduced the percentage of time spent at the peak voltage by a small amount), using the same ramping slope when the switching time is shortened to 0.25 s will reduce the percentage of time spent at the peak voltage by a very significant amount (as depicted in FIGS. 17A/B). Moreover, the situation would be even worse if the interval that the AC voltage is applied to either the LR or AP transducer arrays is reduced below 0.20 s, in which case the peak voltage (and corresponding peak field strength) would never be reached.

Figure 18:
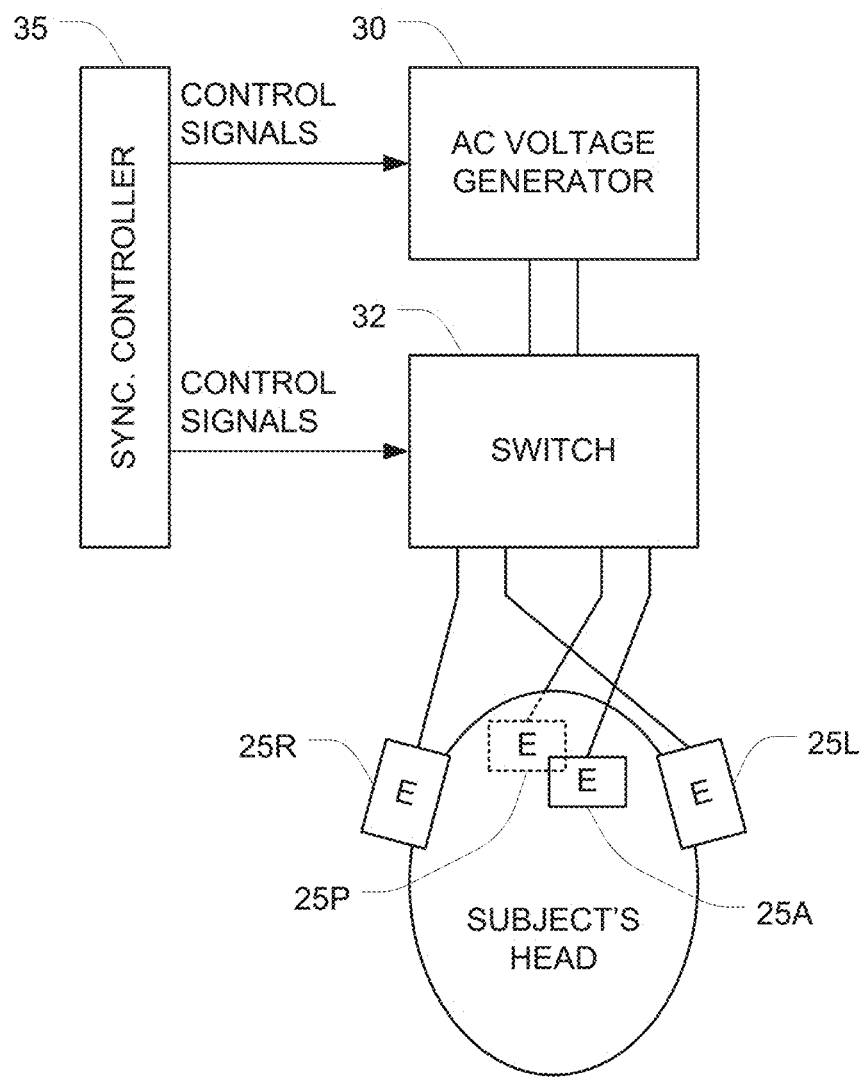
FIG. 18 depicts an embodiment that synchronizes the operation of an AC voltage generator and a switch.

The FIG. 18 embodiment uses a different approach for avoiding spikes that resemble the spike 532 depicted in FIG. 15. More specifically, the FIG. 18 embodiment has an AC voltage generator 30 and a switch 32, and synchronization between those two functional blocks is relied on to avoid spikes, as described below in connection with FIGS. 19-23. In some preferred embodiments, the AC voltage generator 30 in FIG. 18 is implemented using the approaches described above in connection with FIGS. 1-7. The switch 32 is configured to either (a) route the output of the AC voltage generator 30 to the left and right transducer arrays (25L/R) in response to a first state of its control input; (b) route the output of the AC voltage generator 30 to the anterior and posterior transducer arrays (25A/P) in response to a second state of its control input; or (c) remain off in response to a third state of its control input. The switch 32 may be implemented using any of a variety of approaches that will be apparent to persons skilled in the relevant arts, including but not limited to field effect transistors, solid-state relays, etc.

In the illustrated embodiment, synchronization between the AC voltage generator 30 and the switch 32 is implemented using a synchronization controller 35 that is programmed to send control signals to the AC voltage generator 30 and/or the switch 32, to orchestrate those components so that the signals described below are generated with the time relationships described below. A variety of alternative approaches for synchronizing the AC voltage generator 30 and the switch 32 may be used. For example, synchronization may be achieved by allowing the AC voltage generator 30 to run freely and adjusting the switching time of the switch 32 (as described below in connection with FIG. 20). Alternatively, synchronization may be achieved by allowing the switch 32 to switch automatically, and turning off the AC voltage generator 30 prior to each switching event (as described below in connection with FIG. 21). Yet another alternative for achieving synchronization is to control the timing of both the AC voltage generator 30 and the switch 32.

Figure 19:
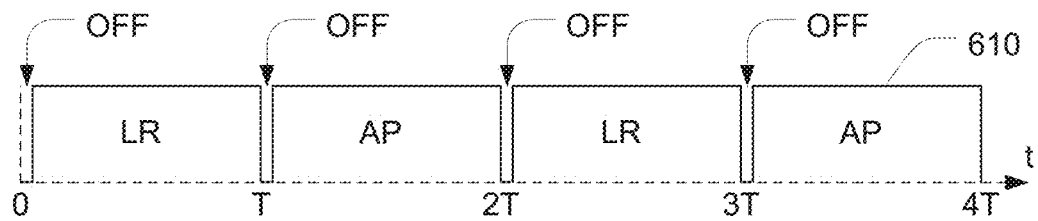
FIG. 19 is a timing diagram that shows the sequencing between the two directions for the FIG. 18 embodiment

FIG. 19 is a timing diagram that shows the sequencing between the two directions LR and AP for the FIG. 18 embodiment. In this embodiment, the switch 32 (a) routes the output of the AC voltage generator 30 to the left and right transducer arrays (25L/R) for a duration T, then (b) routes the output of the AC voltage generator 30 to the anterior and posterior transducer arrays (25A/P) for a duration T, and then repeat steps (a) and (b) in an alternating sequence. A short duration of time (e.g., 5-10 ms) during which the output of the AC voltage generator 30 is not routed to either pair of transducer arrays is interposed between each step (indicated by the label OFF). This may be choreographed by repeatedly adjusting a control input of the switch 32 to cycle through the LR mode, the AP mode, and the OFF mode in the following repeating sequence (1) LR mode, (2) OFF mode, (3) AP mode, and (4) OFF mode.

In this embodiment, the duration T can be much shorter than 1 s, because the output voltage of the voltage generator 30 is not ramped up and down slowly (as it was in the prior art embodiment described above in connection with FIG. 16). Instead, the output of the AC voltage generator 30 either stays at its full value constantly (as described below in connection with FIG. 20) or jumps to its full value immediately after the switch 32 switches states (as described below in connection with FIG. 21). In either case, the signal that is applied to the transducer arrays 25A/P, 25L/R will be at its full value the vast majority of the time (e.g., >90% or >95% of the time). And keeping the TTFields stronger for a larger percentage of time can advantageously improve the efficacy of the TTFields treatment. In some embodiments, the duration T is greater than 20 ms. In some embodiments, the duration T is between 0.1 and 0.5 s. In some embodiments, the duration T is between 0.2 and 0.3 s. Notably, in contrast to the situation described above in connection with FIG. 17A/B, the system operates at its full output voltage for a large percentage of time regardless of how short the duration of T is.

Figure 20:
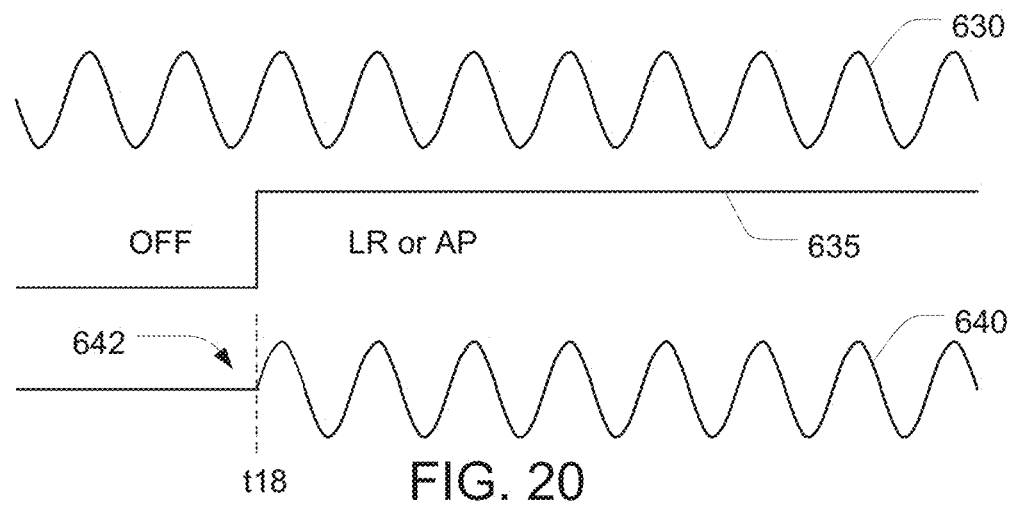
FIG. 20 depicts a first approach for achieving synchronization between the AC voltage generator and the switch in the FIG. 18 embodiment that operates by precisely coordinating the switching of the switch.

FIG. 20 depicts a first approach for achieving synchronization between the AC voltage generator 30 and the switch 32 that operates by controlling timing of transitions of the switch 32 from the OFF state to either the LR state or the AP state (indicated by trace 635) so that the transitions coincide with windows of time during which the instantaneous magnitude of the output of the AC voltage generator is small enough so that jumping from the OFF state to the small voltage will not cause the subject who is being treated to experience a perceptible sensation.

The voltage threshold that results in perception may vary from person to person, and may also depend on which portions of the body make contact with the transducer arrays. For example, on various portions of the body, jumps from the OFF state to either 1V, 1.5V, 2 V, 2.5 V, 3 V, 3.5 V, 4 V, 4.5 V, or 5 V will not be perceptible. So to prevent the switching from causing a perceptible sensation, transitions from the OFF state to either the LR state or the AP state should be timed to coincide with windows of time during which the instantaneous output magnitude of the AC voltage generator is less than or equal to those thresholds. In this approach, the output voltage of the AC voltage generator 30 can remain at its full steady-state value 100% of the time, as depicted by trace 630. In some preferred embodiments, the transitions occur when the instantaneous output of the AC voltage generator is less than 1 V in magnitude.

Assume, for example, that the threshold of perceptibility for a given subject is 5 V, and that the output of the AC voltage generator 30 is 100 V pk-pk (which means that the instantaneous output value of the AC voltage generator 30 will range between +50 and −50 V). The instantaneous output of the AC voltage generator will be less than 5 V in magnitude for the first 5.7° of each 360° cycle, for the middle 11.4° of each cycle, and for the last 5.7° of each cycle. By restricting the switching of the switch 32 from the OFF state to either the LR state or the AP state to these specific windows of time, the signal 640 that is applied to the transducer arrays (25L/R or 25A/P) will never have any spikes that are larger than 5 V in magnitude, which means that they will not be perceptible to the subject. Note that when the AC voltage generator is operating at 200 kHz, 11.4° corresponds to 0.16 μs, and this window is sufficiently long to facilitate synchronization by aligning the switching of the switch 32 to the specific windows of time identified in this paragraph.

In some preferred embodiments, the switching of the switch 32 from the OFF state to either the LR state or the AP state is restricted to those windows of time in which the instantaneous output of the AC voltage generator is less than 1 V in magnitude). Assuming the same 100 V pk-pk output voltage, the instantaneous output of the AC voltage generator will be less than 1 V in magnitude in the first 1.1° of each cycle, in the middle 2.2° of each cycle, and in the last 1.1° of each cycle. By restricting the switching of the switch 32 from the OFF state to either the LR state or the AP state to these specific windows of time, the signal 640 that is applied to the transducer arrays (25L/R or 25A/P) will never have any spikes that are larger than 1 V in magnitude. As would be appreciated by those skilled in the art, timing of switch 32 can be similarly adjusted for other threshold values.

In the example illustrated in FIG. 20, the output voltage of the AC voltage generator 30 remains at its full steady-state value 100% of the time, as depicted by trace 630. In this situation, the signal 640 that is applied to the transducer arrays (25L/R or 25A/P) jumps instantly to its full steady-state output voltage as soon as it is turned on. The signal that is applied to the transducer arrays 25A/P, 25L/R will therefore be at its full value almost all the time. And as noted above, keeping the TTFields stronger for a larger percentage of time can advantageously improve the efficacy of the TTFields treatment. Note, however, that the output voltage of the AC voltage generator 30 during the very beginning of the LR or AP state is not critical, and in alternative embodiments it is acceptable if the AC voltage generator's output voltage dips to some extent. But the output of the AC voltage generator 30 should preferably reach at least 80% of the AC voltage generator's steady-state output voltage within 20 ms after the electronic switch switches from the OFF state to either the LR state or the AP state. In some preferred embodiments, this occurs within 5 ms. And in some preferred embodiments, this occurs within 1 ms.

A similar synchronization of the switching of the switch 32 to the low-magnitude portions (i.e., less than or equal to 1V, 1.5V, 2 V, 2.5 V, 3 V, 3.5 V, 4 V, 4.5 V, or 5 V in magnitude) of the AC voltage generator's output sinusoid is preferably implemented when the switch 32 switches from either the LR state or the AP state back to the OFF state.

Figure 21:
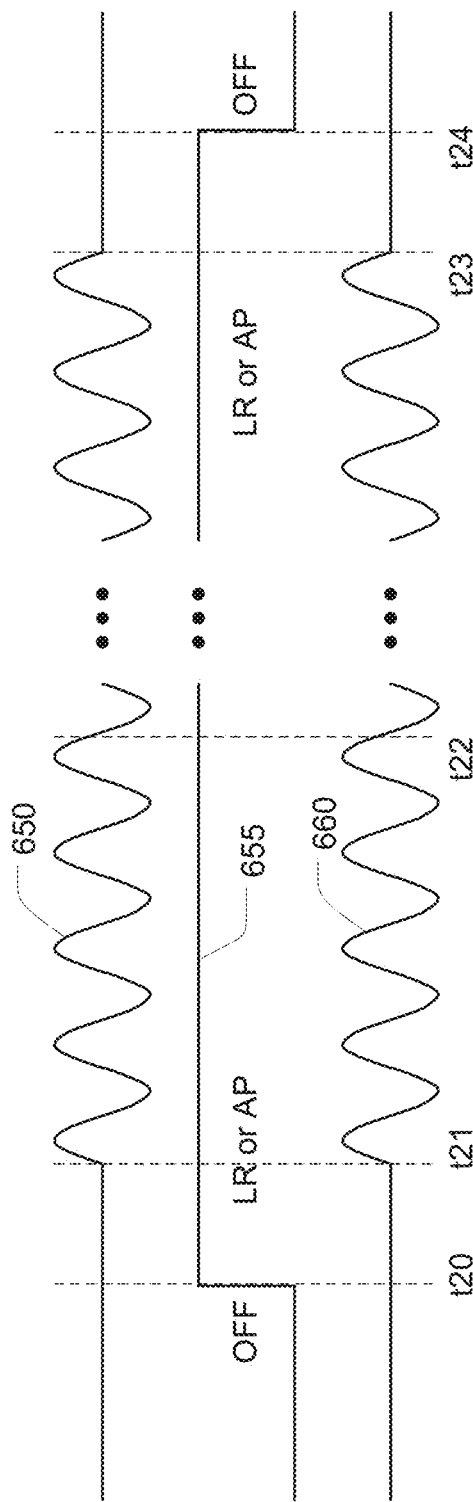
FIG. 21 depicts a second approach for achieving synchronization between the AC voltage generator and the switch in the FIG. 18 embodiment that operates by controlling the output of the AC voltage generator.

FIG. 21 depicts a second approach for achieving synchronization between the AC voltage generator 30 and the switch 32 in FIG. 18. This approach operates by reducing the instantaneous output voltage of the AC voltage generator 30 to less than 5 V in magnitude prior to switching of the switch 32 from the OFF state to either the LR state or the AP state, in order to prevent spikes from appearing on the conductors that lead to the transducer arrays 25L/R and 25A/P when the switch 32 switches states. In some preferred embodiments, the instantaneous output voltage of the AC voltage generator 30 is reduced to less than 1 V (e.g., to 0 V) in magnitude prior to switching of the switch 32.

Reducing the output voltage of the AC voltage generator 30 to 0 V is easy to accomplish when any of the embodiments described above in connection with FIGS. 1-6 and 10-12 are used as the AC voltage generator. For example, when the FIGS. 1 and 2 AC voltage generator is used, its output can be set to zero by ensuring that neither the first control signal nor the second control signal is applied to the control input of the power switcher 60, which means that all the switches (i.e., switches 61-64) in the power switcher 60 will remain off. Similarly, when the FIGS. 5 and 6 AC voltage generator is used, its output can be set to zero by sending a control signal to the power switcher 60B that causes all the switches (i.e., switches 61-66) in the power switcher 60B to switch off.

In FIG. 21, the upper trace 650 depicts the output of the AC voltage generator 30; the middle trace 655 depicts the state of the switch 32; and the lower trace 660 depicts one of the outputs (LR or AP) of the switch 32. Assume that the switch 32 starts in the OFF state, and that at t20 the switch 32 will be set to route the output of the AC voltage generator 30 to either the LR pair of transducer arrays 25L/R or the AP pair of transducer arrays 25A/P. At some time prior to t20, control signals are sent to the AC voltage generator 30 to reduce the output voltage of the AC voltage generator 30 to zero. Because the output of the AC voltage generator 30 is 0 V when the switch 32 is switched at t20, a spike will not appear on the conductors that lead to the transducer arrays 25L/R and 25A/P at that time.

A short interval of time (e.g., <0.1 ms) later, at t21, the synchronization controller 35 (see FIG. 18) begins sending control signals to the AC voltage generator 30 (e.g., as described above in connection with FIGS. 1-6 and 10-12), which causes the AC voltage generator 30 to begin generating the sinusoid 650. Due to the construction of the AC voltage generator (e.g., as described above in connection with FIGS. 1-6 and 10-12), and in particular the output filter 80/80B in the FIG. 1-5 embodiments, the AC voltage generator 30 will not introduce any spikes on the output 650 at t21, so no spikes will propagate to the output 660. And because the switch 32 is already settled into its current state, the switch 32 will not introduce any spikes on the output 660 (which is fed to the transducer arrays 25L/R or 25A/P) at t21.

Figure 22:
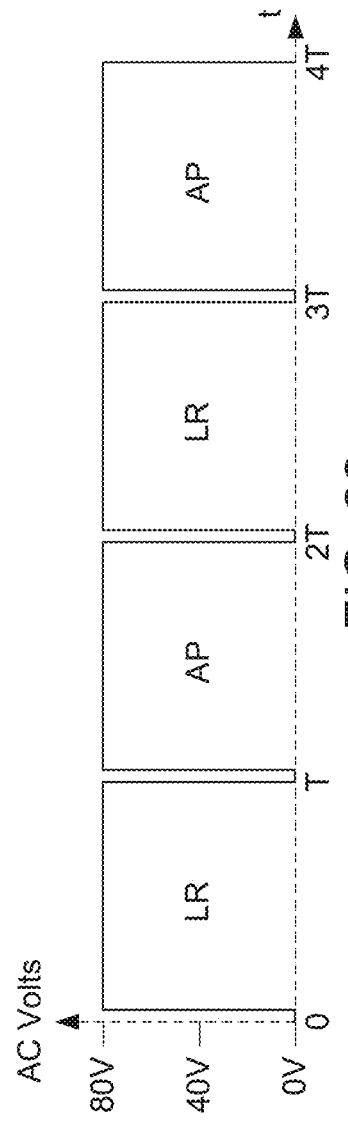
FIG. 22 depicts how the output of the AC voltage generator jumps immediately to its full steady-state output voltage when the FIG. 21 approach is used.

Notably, as depicted in FIG. 21, the output voltage 650 of the AC voltage generator 30 preferably jumps immediately to its full steady-state output voltage, with no ramp-up period. The signal that is applied to the transducer arrays 25A/P, 25L/R will therefore be at its full value almost all the time. And as noted above, keeping the TTFields stronger for a larger percentage of time can advantageously improve the efficacy of the TTFields treatment. FIG. 22 depicts the immediate jump to the full steady-state output voltage on a longer timescale, and this figure stands in sharp contrast to the prior art configuration depicted in FIG. 16. Note, however, that the output voltage of the AC voltage generator 30 during the very beginning of the LR or AP state is not critical, and in alternative embodiments it is acceptable if the AC voltage generator's output voltage does not jump immediately to its full steady-state voltage. But the output of the AC voltage generator 30 should preferably reach at least 80% of the AC voltage generator's steady-state output voltage within 20 ms after the electronic switch switches from the OFF state to either the LR state or the AP state. In some preferred embodiments, this occurs within 5 ms. And in some preferred embodiments, this occurs within 1 ms.

FIG. 21 also depicts an exemplary approach for synchronizing the AC voltage generator 30 and the switch 32 when the time arrives to switch from either the LR state or the AP state to the OFF state. At time t22, the AC voltage generator 30 is generating a sinusoid at its full steady-state output voltage, and the switch 32 remains set to route the output of the AC voltage generator 30 to either the LR pair of transducer arrays 25L/R or the AP pair of transducer arrays 25A/P. At time t23, the controller stops generating the signals (described above in connection with FIGS. 1-6 and 10-12) to the power switcher 60/60B, which causes the output of the AC voltage generator 30 to drop to 0V. And due to the construction of the AC voltage generator described above, no spikes will appear on the output 650 at t23, which means that no spikes will appear on the output 660 of the switch 32. A short interval of time later (e.g., <0.1 ms), at t24, the switch 32 is set to the OFF state. And because the output of the AC voltage generator 30 is 0 V at t24, no spikes will be introduced onto the conductors that run between the switch 32 and the transducer arrays 25 at t24.

In the embodiments described above in connection with FIGS. 18 and 19, the switch 32 (a) routes the output of the AC voltage generator 30 to the left and right transducer arrays (25L/R) for a duration T, then (b) routes the output of the AC voltage generator 30 to the anterior and posterior transducer arrays (25A/P) for a duration T, and then repeat steps (a) and (b) in an alternating sequence. A short duration of time (e.g., 5-10 ms) during which the output of the AC voltage generator 30 is not routed to either pair of transducer arrays is interposed between each step. This is choreographed by repeatedly adjusting a control input of the switch 32 to cycle through the LR mode, the AP mode, and the OFF mode in the following repeating sequence (1) LR mode, (2) OFF mode, (3) AP mode, and (4) OFF mode.

In a variation of these embodiments, the OFF mode (i.e., the short duration of time during which the output of the AC voltage generator 30 is not routed to either pair of transducer arrays) is omitted. With this variation, the switch 32 (a) routes the output of the AC voltage generator 30 to the left and right transducer arrays (25L/R) for a duration T, then (b) routes the output of the AC voltage generator 30 to the anterior and posterior transducer arrays (25A/P) for a duration T, and then repeat steps (a) and (b) in a two-step alternating sequence. This is choreographed by repeatedly adjusting a control input of the switch 32 to cycle through the LR mode and the AP mode in the following repeating sequence (1) LR mode, (2) AP mode.

In this variation where the OFF mode is omitted, the duration T can also be much shorter than 1 s for the same reasons as described above. And here again, in contrast to the situation described above in connection with FIG. 17A/

B, the system operates at its full output voltage for a large percentage of time (e.g., 100% of the time) regardless of how short the duration of T is.

Transitions of the switch 32 from the LR state to the AP state and from the AP state to the LR state are timed so that the transitions coincide with windows of time during which the instantaneous magnitude of the output of the AC voltage generator is small enough so as not to cause the subject who is being treated to experience a perceptible sensation. More specifically, transitions between the LR and AP states should be timed to coincide with windows of time during which the instantaneous output magnitude of the AC voltage generator is less than or equal to the same thresholds noted above in the FIG. 18-20 embodiments that include the OFF state (e.g., in the first 1.1° of each cycle, in the middle 2.2° of each cycle, and in the last 1.1° of each cycle).

Figure 23:
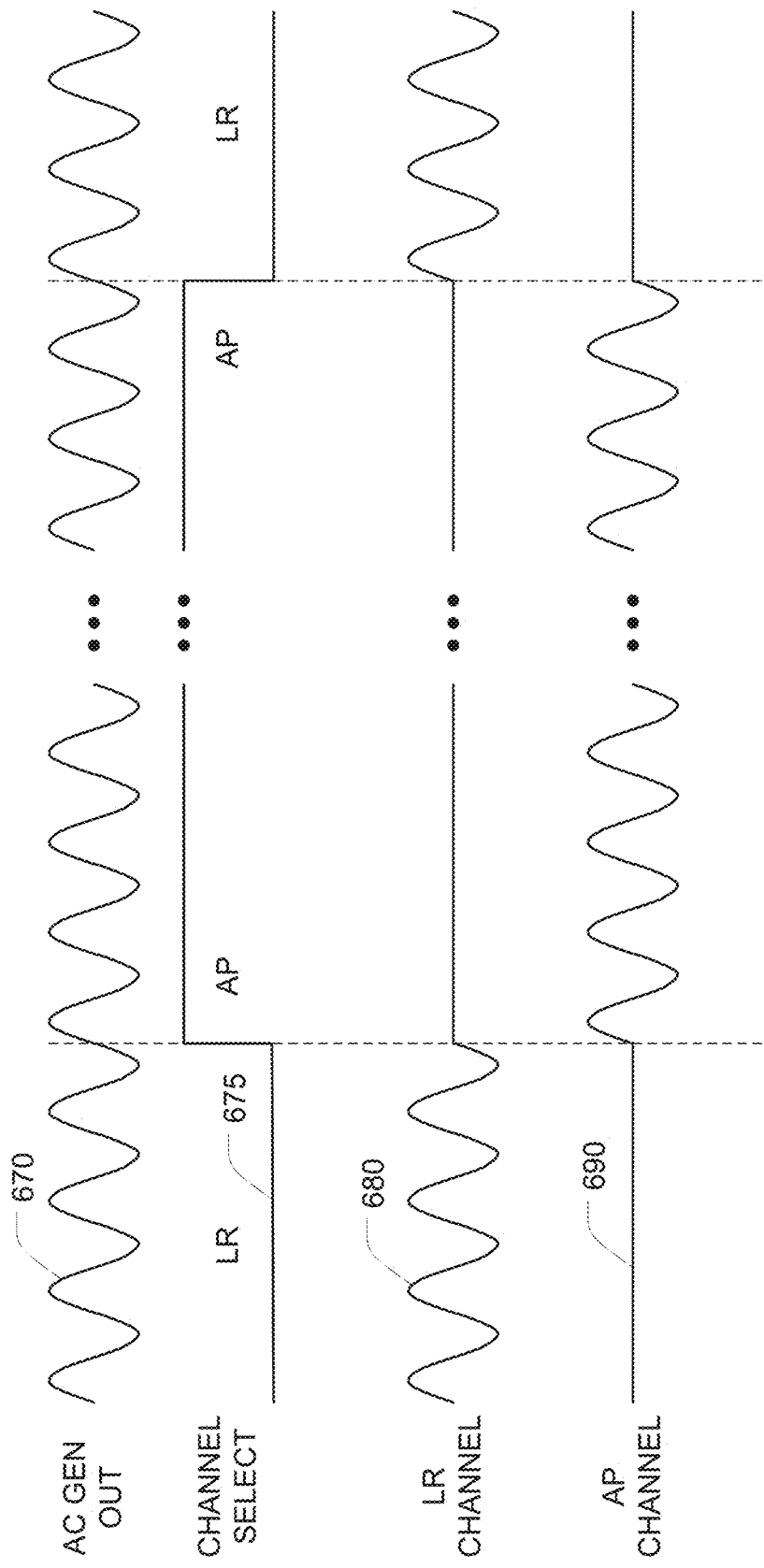
FIG. 23 depicts another approach for achieving synchronization between the AC voltage generator and the switch in the FIG. 18 embodiment that operates by precisely coordinating the switching of the switch.

FIG. 23 depicts an example of timing that synchronizes transitions of the switch 32 (shown in FIG. 18) between the LR and AP states (indicated by trace 675 in FIG. 23) with the output (indicated by trace 670) of the AC voltage generator 30 (shown in FIG. 18) so that the transitions between the LR and AP states coincide with windows of time during which the instantaneous magnitude of the output of the AC voltage generator 30 (trace 675) is close to zero (e.g., <5 V or <1 V).

The embodiments described above in connection with FIGS. 18-22 advantageously make it possible to drive the transducer arrays at full power for a much larger percentage of the time than was possible in the prior art systems, without fear of introducing voltage spikes that could create an unpleasant sensation in the person being treated. And driving the transducer arrays at full power can advantageously increase the efficacy of treatment using TTFields.

Finally, although the embodiments described above in connection with FIGS. 18-23 discuss switching the AC voltage between a first pair of transducer arrays positioned anterior/posterior of the relevant body part and a second pair of transducer arrays positioned front/back of the relevant body part, this approach can be extended to more than two pairs of transducer arrays. For example, the third pair of transducer arrays may be positioned above/below the relevant body part, in which case the AC voltage would be switched between the first, second, and third pairs of transducer arrays in a repeating sequence in a manner that is similar to the switching described above in connection with FIGS. 18-23.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for generating AC electrical signals for application to a first pair of electrodes and a second pair of electrodes, the apparatus comprising:
    an AC voltage generator having an output;
    an electronic switch having an input that receives the output of the AC voltage generator, a first power output, and a second power output, wherein the electronic switch is configured to (a) operate in a first mode that routes the output of the AC voltage generator to the first power output, and (b) operate in a second mode that routes the output of the AC voltage generator to the second power output, and wherein the electronic switch is further configured to cycle through a repeating sequence that includes the first mode and the second mode; and
    a controller configured to synchronize the operation of the AC voltage generator and the electronic switch such that switching of the electronic switch to either the first mode or the second mode is restricted to windows of time that correspond to the first 5.7°, the middle 11.4°, and the last 5.7° of each 360° cycle of the AC voltage generator.

2. The apparatus of claim 1, wherein the electronic switch is further configured to (c) operate in a third mode in which the output of the AC voltage generator is not routed to either the first power output or the second power output, and (d) cycle through the first mode, the second mode, and the third mode in the following repeating sequence (1) first mode, (2) third mode, (3) second mode, and (4) third mode.

3. The apparatus of claim 1, wherein the controller is configured to synchronize the operation of the AC voltage generator and the electronic switch such that switching of the electronic switch to either the first mode or the second mode is restricted to windows of time that correspond to the first 1.1°, the middle 2.2°, and the last 1.1° of each 360° cycle of the AC voltage generator.

4. The apparatus of claim 1, wherein the AC voltage generator continues to operate at its full steady-state AC output voltage during transitions of the electronic switch to either the first mode or the second mode.

5. The apparatus of claim 1, wherein the controller synchronizes the operation of the AC voltage generator and the electronic switch by controlling the AC voltage generator so that the output of the AC voltage generator is turned off whenever a transition of the electronic switch occurs.

6. The apparatus of claim 1, wherein the controller synchronizes the operation of the AC voltage generator and the electronic switch by both (a) controlling timing of transitions of the electronic switch so that the transitions coincide with windows of time that correspond to the first 5.7°, the middle 11.4°, and the last 5.7° of each 360° cycle of the AC voltage generator and (b) controlling the AC voltage generator so that the output of the AC voltage generator is turned off whenever a transition of the electronic switch occurs.

7. The apparatus of claim 1, wherein the electronic switch is configured to cycle through the first mode and the second mode in the following repeating sequence (1) first mode, (2) second mode, and wherein the electronic switch is configured to switch directly from the first mode to the second mode and to switch directly from the second mode to the first mode.

8. An apparatus for generating AC electrical signals for application to a first pair of electrodes and a second pair of electrodes, the apparatus comprising:
    an AC voltage generator having an output;
    an electronic switch having an input that receives the output of the AC voltage generator, a first power output, and a second power output, wherein the electronic switch is configured to (a) operate in a first mode that routes the output of the AC voltage generator to the first power output, and (b) operate in a second mode that routes the output of the AC voltage generator to the second power output, and wherein the electronic switch is further configured to cycle through a repeating sequence that includes the first mode and the second mode; and
    a controller configured to synchronize the operation of the AC voltage generator and the electronic switch such that switching of the electronic switch to either the first mode or the second mode occurs only during portions of a 360° cycle of the output of the AC voltage generator that have a magnitude that is below a magnitude at which a subject to be treated is expected to begin to experience a perceptible sensation.

9. The apparatus of claim 8, wherein the electronic switch is further configured to (c) operate in a third mode in which the output of the AC voltage generator is not routed to either the first power output or the second power output, and (d) cycle through the first mode, the second mode, and the third mode in the following repeating sequence (1) first mode, (2) third mode, (3) second mode, and (4) third mode.

10. The apparatus of claim 8, wherein the controller is configured to synchronize the operation of the AC voltage generator and the electronic switch such that the instantaneous output of the AC voltage generator is less than 1 V in magnitude whenever the electronic switch switches to either the first mode or the second mode.

11. The apparatus of claim 8, wherein the AC voltage generator continues to operate at its full steady-state AC output voltage during transitions of the electronic switch to either the first mode or the second mode.

12. The apparatus of claim 8, wherein the controller synchronizes the operation of the AC voltage generator and the electronic switch by controlling timing of transitions of the electronic switch so that the transitions coincide with windows of time during which the instantaneous output of the AC voltage generator has a magnitude that is below the magnitude at which a subject to be treated is expected to begin to experience perceptible sensation.

13. The apparatus of claim 8, wherein the controller synchronizes the operation of the AC voltage generator and the electronic switch by controlling the AC voltage generator so that the output of the AC voltage generator is turned off whenever a transition of the electronic switch occurs.

14. The apparatus of claim 8, wherein the controller synchronizes the operation of the AC voltage generator and the electronic switch by both (a) controlling timing of transitions of the electronic switch so that the transitions coincide with windows of time during which the instantaneous output of the AC voltage generator has a magnitude that is below the threshold and (b) controlling the AC voltage generator so that the output of the AC voltage generator is turned off whenever a transition of the electronic switch occurs.

15. The apparatus of claim 8, wherein the electronic switch is configured to cycle through the first mode and the second mode in the following repeating sequence (1) first mode, (2) second mode, and wherein the electronic switch is configured to switch directly from the first mode to the second mode and to switch directly from the second mode to the first mode.

16. A method for generating AC electrical signals using an AC voltage generator and an electronic switch, the method comprising:
   switching the electronic switch to a first state that routes the output of the AC voltage generator to a first output;
   switching the electronic switch to a second state that routes the output of the AC voltage generator to a second output; and
   cycling through a repeating sequence that includes switching the electronic switch to the first state and switching the electronic switch to the second state,
   wherein the switching of the electronic switch to either the first state or the second state is restricted to windows of time that correspond to the first 5.7°, the middle 11.4°, and the last 5.7° of each 360° cycle of the AC voltage generator's output.

17. The method of claim 16, wherein the switching of the electronic switch to either the first state or the second state is restricted to windows of time that correspond to the first 1.1°, the middle 2.2°, and the last 1.1° of each 360° cycle of the AC voltage generator.

18. The method of claim 16, wherein the AC voltage generator continues to operate at its full steady-state AC output voltage during switching of the electronic switch to either the first state or the second state.

19. The method of claim 16, wherein the electronic switch is configured to switch directly from the first state to the second state and to switch directly from the second state to the first state.

* * * * *